United States Patent
Cooper et al.

(10) Patent No.: US 12,358,905 B2
(45) Date of Patent: Jul. 15, 2025

(54) METHODS FOR MAKING THIAZOLYPYRAZOLE CARBOXYLIC ACIDS AND INTERMEDIATES THEREFOR

(71) Applicant: Bantam Pharmaceutical, LLC, New York, NY (US)

(72) Inventors: Alan Cooper, Kenilworth, NJ (US); Paul O'Shea, Princeton, NJ (US); Narayanan Anantha, Greensboro, NC (US)

(73) Assignee: Bantam Pharamceutical, LLC, New York, NY (US)

( * ) Notice: Subject to any disclaimer, the term of this patent is extended or adjusted under 35 U.S.C. 154(b) by 743 days.

(21) Appl. No.: 17/614,969

(22) PCT Filed: May 29, 2020

(86) PCT No.: PCT/US2020/035341
§ 371 (c)(1),
(2) Date: Nov. 29, 2021

(87) PCT Pub. No.: WO2020/243582
PCT Pub. Date: Dec. 3, 2020

(65) Prior Publication Data
US 2022/0267314 A1    Aug. 25, 2022

Related U.S. Application Data

(60) Provisional application No. 62/855,652, filed on May 31, 2019.

(51) Int. Cl.
*C07D 417/04* (2006.01)

(52) U.S. Cl.
CPC .................. *C07D 417/04* (2013.01)

(58) Field of Classification Search
CPC ..................................... C07D 417/04
See application file for complete search history.

(56) References Cited

FOREIGN PATENT DOCUMENTS

WO    2018102452 A2    6/2018

OTHER PUBLICATIONS

Cooper et al., 27 Bioorg. & Med. Chem. Letts, 4471-4477 (2017) (Year: 2017).*
PCT International Search Report and Written Opinion, Application No. PCT/US2020/035341, mailed Sep. 7, 2021, 11 pages.
Cooper, Alan B., Stephane Ciblat, Gerald Shipps, Jedd Levine, Matthew Kostura, Vibha Oza, Lea Constantineau-Forget et al. "1-Thiazol-2-yl-N-3-methyl-1H-pyrozole-5-carboxylic acid derivatives as antitumor agents." Bioorganic & medicinal chemistry letters 27, No. 18 (2017): 4471-4477.

* cited by examiner

*Primary Examiner* — Timothy R Rozof
(74) *Attorney, Agent, or Firm* — McDonnell Boehnen Hulbert & Berghoff LLP

(57) ABSTRACT

This disclosure relates generally to improved methods of preparing pyrazolylthiazole-containing compounds and their intermediates.

20 Claims, No Drawings

METHODS FOR MAKING THIAZOLYPYRAZOLE CARBOXYLIC ACIDS AND INTERMEDIATES THEREFOR

CROSS-REFERENCE TO RELATED APPLICATIONS

This application is a U.S. National Stage entry of International Patent Application no. PCT/US2020/035341, filed May 29, 2020, which claims the benefit of priority of U.S. Provisional Patent Application No. 62/855,652, filed May 31, 2019, which is hereby incorporated herein by reference in its entirety.

BACKGROUND OF THE DISCLOSURE

Field of the Disclosure

This disclosure relates generally to improved methods of preparing pyrazolylthiazole-containing compounds, and intermediates useful therefor.

Technical Background

Cancer, an uncontrolled proliferation of cells, is a multifactorial disease characterized by tumor formation, growth, and in some instances, metastasis. In the United States this year, over 1.5 million people will be diagnosed with cancer, and more than 500,000 people will die from cancer. Overall it is estimated that at least one in three people will develop some form of cancer during their lifetime. There are more than 200 different histopathological types of cancer, with breast, lung, colorectal, and prostate accounting for over half of all new cases in the U.S. Current cancer therapies vary depending upon the localization and stage of the cancer but generally include a combination of surgery, systemic therapy, radiation therapy, and chemotherapy. Despite the effort that has been devoted to the development of anticancer strategies, many of them remain inefficacious for specific cancers The uncontrolled cell proliferation that represents the essence of cancer involves not only deregulated control of cell proliferation but also corresponding adjustments of energy metabolism in order to fuel cell growth and division. The reprogramming of cell metabolism is emerging as an important molecular hallmark of cancer cells. Under aerobic conditions, normal cells process glucose, first to pyruvate via glycolysis in the cytosol and thereafter to carbon dioxide in the mitochondria; under anaerobic conditions, glycolysis is favored and relatively little pyruvate is dispatched to the oxygen-consuming mitochondria. When growth factors and nutrients are abundant, oncogenic signaling pathways direct enhanced metabolism leading to increased synthesis of macromolecules such as lipids, proteins and nucleic acids. The net effect is the support of cell growth and proliferation. During tumor formation, however, a harsh, anoxic, nutrient deprived environment exists that challenges the cell and its ability to maintain metabolic homeostasis. Cancer cells can reprogram their glucose metabolism, and thus their energy production, by limiting their energy metabolism largely to glycolysis, which was seen by early biochemists as primitive and inefficient.

Despite these early beliefs, the metabolic signatures of cancer cells are not passive responses to damaged mitochondria, but result from oncogene-directed metabolic reprogramming required to support anabolic growth. Oncogene mutations that allow for increased and more efficient utilization of scarce nutrients present unique targets in treatment of cancer.

Particularly useful ring-substituted pyrazolylthiazole compounds for the treatment of cancer were disclosed in International Publications No. WO 2018/102452 and WO 2018/102453, each of which is hereby incorporated herein by reference in its entirety. One example of such a compound is 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid. These compounds are believed to be active against cancer cells by arresting the cell cycle at the G0/G1 phase, and thereby inducing apoptosis of a cancer cell, and are also believed to inhibit glutathione synthesis in a cancer cell. As a result, the ring-substituted pyrazolylthiazole compounds show promise for treatment of cancer, and there is a need for efficient methods to prepare these compounds.

SUMMARY OF THE DISCLOSURE

The disclosure provides improved methods of preparing ring-substituted pyrazolylthiazole compounds, such as compounds of formula (I):

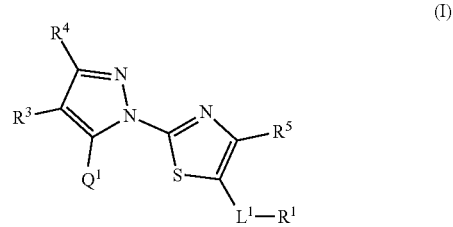

optionally in the form of a pharmaceutically acceptable salt or N-oxide, and/or a solvate or hydrate, wherein $L^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{12}$NR$^6$— and —NR$^6$S(O)$_{1-2}$µ;

$R^1$ is selected from the group consisting of $C_1$-$C_8$ alkyl, $C_1$-$C_8$ alkenyl and $C_1$-$C_8$ alkynyl, each unsubstituted or fluorinated;

Q is selected from the group consisting of —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —S(O)$_2$R$^{2A}$, —N(R$^{2B}$)S(O)$_2$R$^{2A}$, —S(O)$_2$NR$^{2B}$R$^{2A}$, and —C(O)NH—O(C$_1$-$C_3$ alkyl), in which each $R^{2A}$ is independently selected from H, $C_1$-$C_3$ alkyl, and a protecting group, and
each $R^{2B}$ is independently selected from H and $C_1$-$C_3$ alkyl;

$R^3$ is phenyl or heteroaryl each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3D}$), -L$^{3C}$-(heterocloalkyl optionally substituted with 1-5 R$^{3D}$) and (ii) optionally substituted with 1-5 R$^{3E}$, in which
each $L^{3C}$ is a bond, methylene, ethylene, —C(O)—, —S—, —S(O)$_{1-2}$—, —O—, or —NR$^{3G}$—;

each $R^{3D}$ is independently selected from oxo optionally-substituted $C_1$-$C_4$ alkyl, $C_1$-$C_4$ fluoroalkyl, halogen, —CN, —$SF_5$, —$N_3$, —C(O)$R^3$, —$SR^{3F}$, —S(O)$_{1-2}R^{3F}$, —$OR^{3F}$, —$NR^{3G}R^{3F}$, —C(O)$R^{3F}$, —C(O)$NR^{3G}R^{3F}$, —$NR^{3G}$C(O)$R^{3F}$, —C(S)$NR^{3G}R^{3F}$, —$NR^{3G}$C(S)$R^{3F}$, —C(O)$OR^{3F}$, —OC(O)$R^{3F}$, —C(O)$SR^{3F}$, —SC(O)$R^{3F}$, —C(S)$OR^{3F}$, —OC(S)$R^{3F}$, —C(S)$SR^{3F}$, —SC(S)$R^{3F}$, —S(O)$_{1-2}OR^{3F}$, —OS(O)$_{1-2}R^{3F}$, —S(O)$_{1-2}NR^{3G}R^{3F}$, and —$NR^{3G}$S(O)$_{1-2}R^{3F}$;

each $R^{3E}$ is independently selected from oxo, optionally-substituted $C_1$-$C_4$ alkyl, $C_1$-$C_4$ fluoroalkyl, halogen, —CN, —$SF_5$, —$N_3$, —C(O)$R^{3F}$, —$SR^{3F}$, —S(O)$_{1-2}R^{3F}$, —$OR^{3F}$, —$NR^{3G}R^{3F}$, —C(O)$R^{3F}$, —C(O)$NR^{3G}R^{3F}$, —$NR^{3G}$C(O)$R^{3F}$, —C(S)$NR^{3G}R^{3F}$, —$NR^{3G}$C(S)$R^{3F}$, —C(O)$OR^{3F}$, —OC(O)$R^{3F}$, —C(O)$SR^{3F}$, —SC(O)$R^{3F}$, —C(S)$OR^{3F}$, —OC(S)$R^{3F}$, —C(S)$SR^{3F}$, —SC(S)$R^{3F}$, —S(O)$_{1-2}OR^{3F}$, —OS(O)$_{1-2}R^{3F}$, —S(O)$_{1-2}NR^{3G}R^{3F}$, and —$NR^{3G}$S(O)$_{1-2}R^{3F}$;

each $R^{3F}$ is independently selected from H, $C_1$-$C_3$ alkyl, and $C_1$-$C_3$ fluoroalkyl and each $R^{3G}$ is independently selected from H, $C_1$-$C_3$ alkyl, and $C_1$-$C_3$ fluoroalkyl;

$R^4$ is selected from the group consisting of hydrogen, optionally substituted $C_1$-$C_8$ alkyl, optionally substituted $C_1$-$C_8$ alkenyl, and optionally substituted $C_1$-$C_8$ alkynyl; and $R^5$ is aryl, heteroaryl, cycloalkyl, or heterocycloalkyl, each optionally substituted with 1-5 $R^{5E}$, in which each $R^{5E}$ is independently selected from oxo, optionally-substituted $C_1$-$C_4$ alkyl, $C_1$-$C_4$ fluoroalkyl, halogen, —CN, —$SF_5$, —$N_3$, —C(O)$R^{5F}$, —$SR^{5F}$, —S(O)$_{1-2}R^{5F}$, —$OR^{5F}$, —$NR^{5G}R^{5F}$, —C(O)$R^{5F}$, —C(O)$NR^{5G}R^{5F}$, —$NR^{5G}$C(O)$R^{5F}$, —C(S)$NR^{5G}R^{5F}$, —$NR^{1G}$C(S)$R^{5F}$, —C(O)$OR^{5F}$, —OC(O)$R^{5F}$, —C(O)$SR^{5F}$, —SC(O)$R^{5F}$, —C(S)$OR^{5F}$, —OC(S)$R^{5F}$, —C(S)$SR^{5F}$, —SC(S)$R^{5F}$, —S(O)$_{1-2}OR^{5F}$, —OS(O)$_{1-2}R^{5F}$, —S(O)$_{1-2}NR^{3G}R^{5F}$, and —$NR^{5G}$S(O)$_{1-2}R^{5F}$;

each $R^{5F}$ is independently selected from H, $C_1$-$C_3$ alkyl, and $C_1$-$C_3$ fluoroalkyl and each $R^{5G}$ is independently selected from H and $C_1$-$C_3$ alkyl;

wherein each $R^6$ is selected from the group consisting of hydrogen, $C_1$-$C_3$ alkyl, and —C(O)($C_1$-$C_3$ alkyl);

each optionally substituted alkyl, alkenyl and alkynyl is unsubstituted, fluorinated or substituted with one or two hydroxyl groups;

each cycloalkyl has 3-10 ring carbons and is unsaturated or partially unsaturated;

each heterocycloalkyl has 3-10 ring members and 1-3 heteroatoms independently selected from nitrogen, oxygen and sulfur, and is unsaturated or partially unsaturated;

each heteroaryl is a 5-6 membered monocyclic heteroaryl ring having 1-3 heteroatoms independently selected from nitrogen, oxygen and sulfur.

Such methods include coupling pyrazolylthiazole (e.g., of formula (Ia)), optionally in a solvent, with organoboron compounds comprising the desired ring substituent moiety (e.g., comprising an $R^5$ moiety).

The disclosure also provides pyrazolylthiazoles compounds useful as intermediates in the synthesis of compounds of formula (I) and methods of preparing them. Thus, another aspect provides pyrazolylthiazoles of formula (Ia):

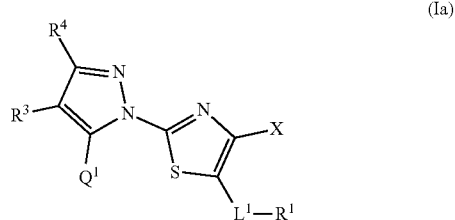

(Ia)

wherein

X is a halogen;

$Q^1$ is selected from the group consisting of —C(O)$OR^{2C}$, —C(O)$NR^{2B}R^{2C}$, —C(O)$NR^{2B}$S(O)$_2R^{2C}$, —C(O)$NR^{2B}$S(O)$_2NR^{2B}R^{2C}$, —S(O)$_2R^{2C}$, —N($R^{2B}$)S(O)$_2R^{2C}$, —S(O)$_2NR^{2B}R^{2C}$, and —C(O)NH—O($C_1$-$C_3$ alkyl), in which each $R^{2B}$ is independently selected from H and $C_1$-$C_3$ alkyl, and each $R^{2C}$ is independently selected from $C_1$-$C_3$ alkyl and a protecting group; and $L^1$, $R^1$, $R^3$, and $R^4$ are as described for formula (I).

Another aspect of the disclosure provides methods of preparing the halopyrazolylthiazoles of the disclosure (e.g. of formula (Ia)). Such methods include reacting a thiazolylhydrazine (e.g., of formula (Ib)) with a dione optionally in a solvent, under conditions sufficient to form a hydrazone; and reacting the hydrazone with a compound of formula $X^1$—$CH_2$-$Q^1$ in which $Q^1$ is as described above and $X^1$ is a halogen or leaving group to obtain the pyrazolylthiazole.

Another aspect provides methods of preparing thiazolylhydrazines (e.g., of formula (Ib)). Such methods include: reacting a dihalothiazole optionally in a solvent, with an aqueous solution of hydrazine to obtain a crude product; and crystallizing the crude product, for example, from hydrocarbon solvent (e.g., hexanes, heptanes, or a combination thereof) to obtain the thiazolylhydrazine.

Another aspect provides a $C_1$-$C_3$ alkyl 1-(4-halo-5-(isopropylthio)thiazol-2-yl)-4-(3-fluorophenyl)-3-methyl-1H-pyrazole-5-carboxylate. One embodiment of this aspect provides ethyl 1-(4-bromo-5-(isopropylthio)thiazol-2-yl)-4-(3-fluorophenyl)-3-methyl-1H-pyrazole-5-carboxylate).

Other aspects and embodiments of the disclosure are evident in view of the detailed description provided herein.

DETAILED DESCRIPTION

The present inventors have found improved and efficient methods of preparing compounds of formula (I). For example, compared to the currently known methods, such as those disclosed in WO 2018/102453, the current methods allow for the preparation of compound 1 in over 30% overall yield compared to 2.5% overall yield disclosed in WO 2018/102453 for the preparation of the same compound. The methods of the disclosure, for example, also provide relatively pure compounds of formula (I) (e.g., at least 98% pure). Yet, in certain embodiments, this purity may be achieved without need to perform chromatography. Because pyrazolylthiazoles of formula (Ia) may be used in methods of preparing the compounds of formula (I) and, in turn, thiazolylhydrazines of formula (Ib) may be used in methods of preparing the pyrazolylthiazoles, the inventors have found it important to also develop efficient methods of preparing pyrazolylthiazoles of formula (Ia) and/or thiazolylhydrazines of formula (Ib).

Thus, one aspect provides improved methods of preparing a thiazolylhydrazines of formula (Ib):

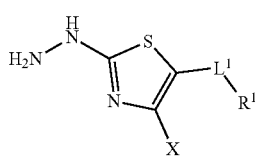

(Ib)

wherein
X is a halogen (e.g., chloro, bromo or iodo);
L$^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{12}$O—, —OS(O)$_{1-2}$—, —S(O)$_{1-2}$NR$^6$— and —NR$^6$S(O)$_{1-2}$—;
R$^1$ is selected from the group consisting of C$_1$-C$_8$ alkyl, C$_1$-C$_8$ alkenyl and C$_1$-C$_8$ alkynyl, each unsubstituted or fluorinated;
wherein
each R$^6$ is selected from the group consisting of hydrogen, C$_1$-C$_3$ alkyl and —C(O)(C$_1$-C$_3$ alkyl);
each optionally substituted alkyl is unsubstituted, fluorinated or substituted with one or two hydroxyl groups;
each cycloalkyl has 3-10 ring carbons and is unsaturated or partially unsaturated;
each monocyclic heteroaryl is a 5-6 membered heteroaryl ring having 1-3 heteroatoms independently selected from nitrogen, oxygen and sulfur,
Such methods include:
reacting a dihalothiazole of formula

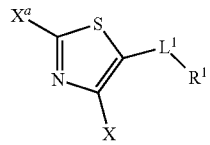

wherein X, R$^1$, and L$^1$ are as described for formula (Ib), and X$^a$ is halogen (e.g., chloro, bromo or iodo), optionally in a solvent, with an aqueous solution of hydrazine to obtain a crude product; and
crystallizing the crude product, for example, from hydrocarbon solvent (e.g., hexanes, heptanes, or a combination thereof) to obtain the thiazolylhydrazine of formula (Ib).

In certain embodiments, X$^a$ is chloro. In certain such embodiments, X is bromo or iodo.

In the methods of preparing the thiazolylhydrazines of formula (Ib), the inventors have found that the use of an amount of hydrazine that is at least 6 molar equivalent, based on the amount of the dihalothiazole of formula (Ic), is advantageous. For example, in certain embodiments the amount of hydrazine is at least 6.25 molar equivalent, e.g., at least 6.5 molar equivalent, or at least 7 molar equivalent, all based on the amount of the dihalothiazole. In certain embodiments, the amount of hydrazine is in the range of 6-20 equivalent based on the amount of dihalothiazole, e.g., 6-15 equivalent, or 7-20 equivalent or 7-15 equivalent.

A variety of polar aprotic solvents are suitable for use in the methods of preparing the thiazolylhydrazine of formula (Ib). Examples include tetrahydrofuran (THF), ethyl acetate, acetone, dimethylformamide (DMF), acetonitrile (MeCN), dimethyl sulfoxide (DMSO), etc. In certain embodiments, the solvent is THF.

Reacting the dihalothiazole with the aqueous solution of hydrazine may be carried out at a variety of temperatures, including at about room temperature. For example, in certain embodiments, the reaction is carried out at a temperature in a range of 20° C. to 25° C., or 20° C. to 23° C. In other embodiments, the dihalothiazole is reacted with the aqueous solution of hydrazine at a temperature in a range of 5° C. to 20° C. In other embodiments, the dihalothiazole is reacted with the aqueous solution of hydrazine is carried out at a temperature in a range of 25° C. to 40° C., e.g., 30° C. to 40° C., or 35° C. to 40° C., or 30° C. to 35° C.

The reaction of the dihalothiazole with the aqueous solution of hydrazine is carried out for a time sufficient to obtain a crude product (i.e., containing crude thiazolylhydrazine). In certain embodiments, the dihalothiazole is reacted with the aqueous solution of hydrazine for at least 10 hours, e.g., at least 20 hours, or at least 24 hours, or at least 48 hours, or at least 72 hours. In certain embodiments, the dihalothiazole is reacted with the aqueous solution of hydrazine for a time in a range of 10 hours to 100 hours, e.g., in a range of 24 hours to 100 hours, or 48 hours to 100 hours, or 72 hours to 100 hours, or 10 hours to 72 hours, or 24 hours to 72 hours, or 48 hours to 72 hours, or 10 hours to 48 hours, or 24 hours to 48 hours. The reaction time and reaction temperature can be selected to provide a crude product having a high amount of crude thiazolylhydrazine.

The crude product is crystallized to obtain the thiazolylhydrazine of formula (Ib). Particularly useful crystallization solvents are hydrocarbon solvents, such as hexanes, heptanes, or a combination thereof. In certain embodiments, the crystallization solvent is hexanes. In certain embodiments, the crystallization solvent is heptanes. The crystallization solvent may be used in any volume sufficient to result in crystal formation. In certain embodiments, the crystallization solvent is used in an amount of about 100% v/v to 300% v/v, e.g., 100% v/v to 200% v/v, or 100% v/v to 150% v/v, or 200% v/v to 300% v/v, or 200% v/v to 250% v/v, or 250% v/v to 300% v/v, based on total volume of the crude product. In certain embodiments, the crystallization solvent is added in an amount of about 50% v/v to 99% v/v, based on total volume of the crude product. In certain embodiments, the crystallization solvent is added in an amount of more than 300% v/v, based on total volume of the crude product.

The disclosure also provides halopyrazolylthiazoles and methods of preparing them. Thus, another aspect of the disclosure provides halopyrazolylthiazoles of formula (Ia):

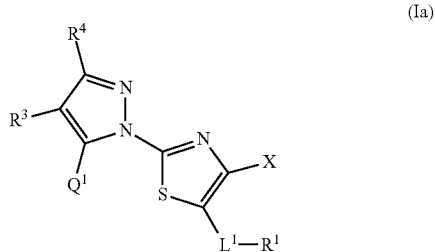

(Ia)

wherein
X is a halogen (e.g., chloro, bromo or iodo);
L$^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;
R$^1$ is selected from the group consisting of C$_1$-C$_8$ alkyl, C$_1$-C$_8$ alkenyl and C$_1$-C$_8$ alkynyl, each unsubstituted or fluorinated;
Q$^1$ is selected from the group consisting of —C(O)OR$^{2C}$, —C(O)NR$^{2B}$R$^{2C}$, —C(O)NR$^{2B}$S(O)$_2$R$^{2C}$, —C(O)NR$^{2B}$S(O)$_2$NR$^{2B}$R$^{2C}$, —S(O)$_2$R$^{2C}$, —N(R$^2$)S(O)$_2$R$^{2C}$, —S(O)$_2$NR$^{2B}$R$^{2C}$, and —C(O)NH—O(C$_1$-C$_3$ alkyl), in which
each R$^{2B}$ is independently selected from H and C$_1$-C$_3$ alkyl, and
each R$^{2C}$ is independently selected from C$_1$-C$_3$ alkyl and a protecting group;
R$^3$ is phenyl or heteroaryl each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^{3E}$, in which
each L$^{3C}$ is a bond, methylene, ethylene, —C(O)—, —S—, —S(O)$_{1-2}$—, —O—, or —NR$^{3G}$—;
each R$^{3D}$ is independently selected from oxo optionally-substituted C$_1$-C$_4$ alkyl, C$_1$-C$_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
each R$^{3E}$ is independently selected from oxo, optionally-substituted C$_1$-C$_4$ alkyl, C$_1$-C$_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
each R$^{3F}$ is independently selected from H, C$_1$-C$_3$ alkyl and C$_1$-C$_3$ fluoroalkyl and
each R$^{3G}$ is independently selected from H, C$_1$-C$_3$ alkyl, and C$_1$-C$_3$ fluoroalkyl; and
R$^4$ is selected from the group consisting of hydrogen, optionally substituted C$_1$-C$_8$ alkyl, optionally-substituted C$_1$-C$_8$ alkenyl and optionally substituted C$_1$-C$_8$ alkynyl;
wherein
each R$^6$ is selected from the group consisting of hydrogen, C$_1$-C$_3$ alkyl and —C(O)(C$_1$-C$_3$ alkyl);
each optionally substituted alkyl, alkenyl and alkynyl is unsubstituted, fluorinated or substituted with one or two hydroxyl groups;
each cycloalkyl has 3-10 ring carbons and is unsaturated or partially unsaturated;
each heterocycloalkyl has 3-10 ring members and 1-3 heteroatoms independently selected from nitrogen, oxygen and sulfur, and is unsaturated or partially unsaturated; and
each heteroaryl is a 5-6 membered monocyclic heteroaryl ring having 1-3 heteroatoms independently selected from nitrogen, oxygen and sulfur.

The methods for preparing a pyrazolylthiazole of formula (Ia) include:
reacting a thiazolylhydrazine of formula (Ib) as described herein with a dione of formula (II)

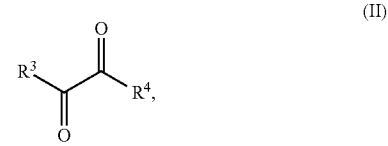

wherein R$^3$ and R$^4$ are as described for formula (Ia), optionally in a solvent, under conditions sufficient to form a hydrazone; and
contacting the hydrazone with an alkylhalogenide of formula X$^1$—CH$_2$-Q$^1$ wherein Q$^1$ is as described for formula (Ia), and X$^1$ is a halogen or a leaving group, to obtain the halopyrazolylthiazole of formula (Ia).

The hydrazone can have the structure (III) below:

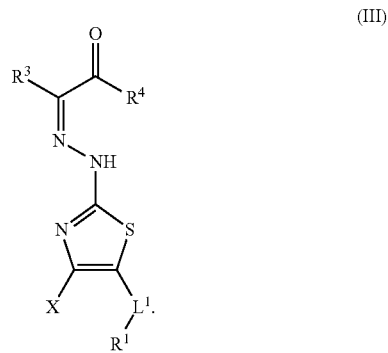

The contacting of the hydrazone with the alkylhalogenide of formula X$^1$—CH$_2$-Q$^1$ can form an intermediate having (IV):

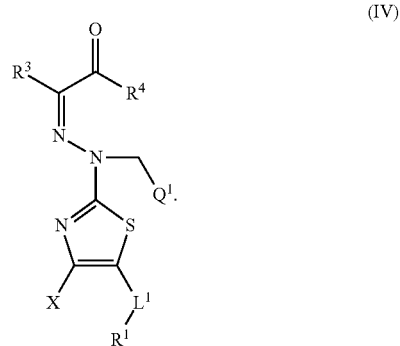

The reaction conditions can be selected such that this intermediate cyclizes with elimination of water to from the halopyrazolylthiazole of formula (Ia).

In certain embodiments, the methods for preparing a halopyrazolylthiazole of formula (Ia) further comprise preparing the thiazolhydrazine of formula (Ib) according to the methods as described herein. For example, in certain embodiments, the methods for preparing a halopyrazolylthiazole of formula (Ia) include:

reacting a dihalothiazole of formula (1c) as described herein, optionally in a solvent, with an aqueous solution of hydrazine to obtain a crude product (i.e., containing crude thiazolylhydrazine);

crystalizing the crude product (e.g., from a hydrocarbon solvent such as hexanes, heptanes, or a combination thereof) to obtain a thiazolylhydrazine of formula (Ib) as described herein;

reading the thiazolylhydrazine of formula (Ib) as described herein with a dione as described herein, optionally in a solvent, under conditions sufficient to form a hydrazone; and reacting the hydrazone with an alkylhalogenide as described herein to obtain the halopyrazolylthiazole of formula (Ia).

The inventors have found that halopyrazolylthiazoles of formula (Ia) where X is Cl, Br or I are advantageous, particularly when used to prepare the compounds of formula (I). In certain embodiments as otherwise described herein, in the halopyrazolylthiazole of formula (Ia) X is Br. In certain embodiments as otherwise described herein, in the halopyrazolylthiazole of formula (Ia) X is Cl. In certain embodiments as otherwise described herein, in the halopyrazolylthiazole of formula (Ia) X is 1.

The inventors have also found that the use of an amount of the dione of at least 1 molar equivalent, based on the amount of the thiazolylhydrazine, is advantageous. For example, the amount of the dione may be at least 1.1 molar equivalent, e.g., at least 1.25 molar equivalent, or at least 1.5 molar equivalent, all based on the amount of the thiazolylhydrazine.

The thiazolylhydrazine and the dione as otherwise described herein can be reacted in a solvent in certain embodiments. For example, suitable solvents include, but are not limited to, dioxane, toluene, THF, DMF, and dichloromethane.

Reacting the thiazolylhydrazine and the dione may be carried out at a variety of temperatures, including at about room temperature. For example, in certain embodiments, the reaction is carried out at a temperature in a range of 20° C. to 25° C., or 20° C. to 23° C. The reaction of the thiazolylhydrazine and the dione may be carried out for a time sufficient to obtain the hydrazone. In certain embodiments, the thiazolylhydrazine is reacted with the dione for at least 8 hours, e.g., at least 10 hours, or at least 12 hours, or at least 14 hours, or at least 16 hours. In certain embodiments, the thiazolylhydrazine is reacted with the dione at about room temperature for a time in a range of 8 hours to 20 hours, e.g., in a range of 8 hours to 16 hours, or 8 hours to 14 hours, or 8 hours to 12 hours, or 8 hours to 10 hours, or 10 hours to 20 hours, or 10 hours to 16 hours, or 10 hours to 14 hours, or 10 hours to 12 hours, or 14 hours to 20 hours, or 14 hours to 18 hours, or 14 hours to 16 hours, or 16 hours to 20 hours, or 16 hours to 18 hours, or 18 hours to 20 hours. Reacting the thiazolylhydrazine and the dione may alternatively be carried out a a temperature above room temperature. For example, the reaction of the thiazolylhydrazine and the dione may be at a temperature of at least 40° C., e.g., at least 45° C., or at least 50° C., or at least 60° C., or at least 65° C. In certain embodiments, the reaction of the thiazolylhydrazine and the dione may be at a temperature in a range of 40° C. to 80° C., e.g., in a range of 40° C. to 70° C., or 40° C. to 60° C., or 40° C. to 50° C., 50° C. to 80° C., or 50° C. to 70° C., or 50° C. to 60° C., or 60° C. to 80° C., or 60° C. to 70° C. In certain embodiments, the thiazolylhydrazine and the dione are reacted at said temperature above room temperature for at least 30 minutes (e.g., at least 45 minutes, or at least 1 hour).

In the methods as described herein, the hydrazone is reacted with the alkylhalogenide as described herein to prepare the halopyrazolylthiazole of formula (Ia). The hydrazone and the alkylhalogenide may be reacted, for example, in presence of an inorganic iodide and a base. The inorganic iodide, in certain embodiments, may be KI or NaI. In certain embodiments, the hydrazone is contacted with the alkylhalogenide in presence of an inorganic iodide that is KI. The base, in certain embodiments, may be a carbonate (such as potassium carbonate, sodium carbonate, cesium carbonate, thallium(I) carbonate, etc.), hydroxides (such as potassium hydroxide, sodium hydroxide, etc.), ethoxides (such as sodium ethoxide, potassium tert-butoxide, thallium(I) ethoxide, etc.), amines (such as trimethylamine, 1,8-diazabicyclo [5.4.0]undec-7-ene, N,N-dimethylethylamine, etc.), hydride (such as sodium hydride and potassium hydride). In certain embodiments, the hydrazone is contacted with the alkylhalogenide in presence of base that is a carbonate (such as potassium carbonate).

In certain embodiments, the inorganic iodide is provided in a catalytic amount. For example, in certain embodiments, the amount of inorganic iodide is no more than 20 mol %, e.g., no more than 15 mol %, or no more than 10 mol %, based on the amount of the hydrazone. In certain embodiments, the amount of inorganic iodide is in a range of 5 mol % to 20 mol %, for example, in a range of 5 mol % to 15 mol %, or in a range of 5 mol % to 10 mol %, or in a range of 8 mol % to 20 mol %, or in a range of 8 mol % to 15 mol %, or in a range of 8 mol % to 12 mol %, or in a range of 8 mol % to 10 mol %, or in a range of 10 mol % to 20 mol %, or in a range of 10 mol % to 15 mol %, based on the amount of the hydrazone.

In certain alternative embodiments, the inorganic iodide may be provided in a stoichiometric amount. For example, in certain embodiments, the amount of inorganic iodide is at least 1 molar equivalent, e.g., at least 1.1 molar equivalent, or at least 1.25 molar equivalent, or at least 1.5 molar equivalent, or at least 2 molar equivalent, based on the amount of the hydrazone.

The hydrazone and the alkylhalogenide may be contacted at a temperature and for a time sufficient to obtain the halopyrazolylthiazole.

For example, in certain embodiments, the hydrazone and the alkylhalogenide are reacted at a temperature of at least 80° C., e.g., at least 85° C., or at least 90° C., or at least 95° C., or at least 100° C., or at least 110° C. In certain embodiments, the hydrazone and the alkylhalogenide are reacted at a temperature in a range of 80° C. to 120° C., for example, in a range of 80° C. to 110° C., or 80° C. to 100° C., or 80° C. to 90° C., or 90° C. to 120° C., or 90° C. to 110° C., or 90° C. to 100° C., or 100° C. to 120° C., or 100° C. to 110° C.

In certain embodiments, the hydrazone and the alkylhalogenide are reacted for at least 8 hours. For example, the hydrazone and the alkylhalogenide may be reacted for at least 10 hours, e.g., at least 12 hours, or at least 14 hours, or at least 16 hours. In another embodiment, the hydrazone and the alkylhalogenide are reacted for a time in a range of 8 hours to 24 hours. For example, in various embodiments, the hydrazone and the alkylhalogenide can be reacted for a time in a range of 8 hours to 20 hours, or 8 hours to 16 hours, or 8 hours to 14 hours, or 8 hours to 12 hours, or 8 hours to 10 hours, or 10 hours to 24 hours, or 10 hours to 20 hours, or 10 hours to 16 hours, or 10 hours to 14 hours, or 10 hours to 12 hours, or 14 hours to 24 hours, or 14 hours to 20 hours, or 14 hours to 18 hours, or 14 hours to 16 hours, or 16 hours to 24 hours, or 16 hours to 20 hours, or 16 hours to 18 hours, or 18 hours to 24 hours, or 18 hours to 20 hours.

As described in more detail below, the reaction of the hydrazone with the alkylhalogenide of formula $X^1$—$CH_2$-$Q^1$ results in substitution of the hydrazone at its substitutable nitrogen with —$CH_2$-$Q^1$; this intermediate then cyclizes through elimination of water to build the pyrazole ring of the halopyrazolylthiazole.

Notably, the reaction of the thiazolylhydrazine with the dione to form the hydrazone (e.g., of formula (III)), the subsequent reaction of the hydrazone with the alkylhalogenide of formula $X^1$—$CH_2$-$Q^1$ to form the substituted hydrazone intermediate (e.g., of formula (IV)), and the cyclization of that hydrazone intermediate to form the halopyrazolylthiazole can be performed without isolation or purification of any intermediate.

The method of preparing the halopyrazolylthiazole of formula (Ia) as described herein, in certain embodiments, may include further crystalizing the halopyrazolylthiazole. For example, the pyrazolylthiazole may be crystalized from an alcohol (such as ethanol) to obtain the compound having purity of at least 98%.

In another aspect, the disclosure provides methods for preparing a compound of formula (I). Such methods include: coupling a halopyrazolylthiazole of formula (Ia) as described herein, optionally in a solvent, with an organoboron-comprising $R^5$ moiety to obtain the compound of formula (I).

In certain embodiments, the methods for preparing a compound of formula (I) further comprise preparing the halopyrazolylthiazole of formula (Ia) according to the methods as described herein. For example, in certain embodiments, the methods for preparing a compound of formula (I) include:
  reacting a thiazolylhydrazine of formula (Ib) as described herein with a dione as described herein, optionally in a solvent, under conditions sufficient to form a hydrazone;
  contacting the hydrazone with an alkylhalogenide as described herein to obtain a halopyrazolylthiazole of formula (Ia); and
  coupling the halopyrazolylthiazole of formula (Ia) as described herein, optionally in a solvent, with an organoboron comprising $R^5$ moiety to obtain the compound of formula (I).

In certain embodiments, the methods for preparing a compound of formula (I) further comprise preparing the halopyrazolylthiazole of formula (Ia) and the thiazolylhydrazine of formula (Ib) according to the methods as described herein. For example, in certain embodiments, the methods for preparing a compound of formula (I) include:
  reacting a dihalothiazole as described herein, optionally in a solvent, with an aqueous solution of hydrazine to obtain a crude product (i.e., containing crude thiazolylhydrazine);
  crystallizing the crude product (e.g., from hydrocarbon solvent such as hexanes, heptanes, or combination thereof) to obtain a thiazolylhydrazine of formula (Ib) as described herein;
  reacting the thiazolylhydrazine of formula (Ib) as described herein with a dione as described herein, optionally in a solvent, under conditions sufficient to form a hydrazone;
  reacting the hydrazone with an alkylhalogenide as described herein to obtain the halopyrazolylthiazole of formula (Ia); and
  coupling the halopyrazolylthiazole of formula (Ia) as described herein, optionally in a solvent, with an organoboron-comprising $R^5$ moiety to obtain the compound of formula (I).

The inventors have found that Suzuki coupling is particularly advantageous to prepare the compound of formula (I). Suzuki coupling is well known to those of skill in the art, and a comprehensive guide of suitable catalysts and coupling conditions may be found in J. P. Wolfe and J. S. Nakhla, *Name Reactions for Homologations. The Suzuki Reaction*. John Wiley & Sons, Inc. (2009), Pt. 1:163-184, incorporated herein by reference in its entirety.

In general, the coupling reaction is carried out in the presence of a catalyst and optionally in presence of a base. Catalysts suitable for Suzuki coupling include palladium catalysts. Examples of palladium catalysts include, but are not limited to, tetrakis(triphenyl-phosphine)palladium(0) ($Pd(PPh_3)_4$), tris(dibenzylideneacetone) dipalladium(0) ($Pd_2(dba)_3$), [1,1'-bis(diphenylphosphino)ferrocene]dichloropalladium(II) ($Pd(dppf)Cl_2$), bis(triphenylphosphine)palladium (II) dichloride ($PdCl_2(PPh_3)_2$), palladium(II) acetate (Pd$(OAc)_2$), $Pd(OAc)_2$/triphenylphosphine ($PPh_3$), $Pd(OAc)_2$/tricyclohexylphosphine ($PCy_3$), $Pd(OAc)_2$/tri(o-tolyl) phosphine ($PTol_3$), and the like. Catalysts suitable for Suzuki coupling may also include nickel catalysts such as bis(1,5-cyclooctadiene)nickel(0) ($Ni(cod)_2$), nickel(II) chloride ethylene glycol dimethyl ether complex ($NiCl_2$-glyme), bis(triphenylphosphine)nickel(II) dichloride ($NiCl_2(PPh_3)_2$), and the like.

The catalyst is provided in an amount sufficient to catalyze the coupling reaction. For example, in certain embodiments the amount of the catalyst is no more than 20 mol %, e.g., no more than 15 mol %, or no more than 10 mol %, or no more than 5 mol %, or no more than 3 mol %, based on the amount of the halopyrazolylthiazole. In certain embodiments, the amount of the catalyst is in a range of 0.1 mol % to 20 mol %, for example, in a range of 0.1 mol % to 15 mol %, or 0.1 mol % to 10 mol %, or 0.1 mol % to 5 mol %, or 0.1 mol % to 1 mol %, or 1 mol % to 20 mol %, or 1 mol % to 15 mol %, or 1 mol % to 10 mol %, or 1 mol % to 5 mol %, or 5 mol % to 20 mol %, or 5 mol % to 15 mol %, or 5 mol % to 10 mol %, based on the amount of the halopyrazolylthiazole. In certain embodiments, the amount of the catalyst is in a range of 8 mol % to 20 mol %, for example, in a range of 8 mol % to 15 mol %, or 8 mol % to 12 mol %, or 8 mol % to 10 mol %, or 10 mol % to 20 mol %, or 10 mol % to 15 mol %, or 15 mol % to 20 mol %, based on the amount of the halopyrazolylthiazole.

Suitable bases used in Suzuki coupling include, for example, carbonates (e.g., potassium carbonate, sodium carbonate, cesium carbonate, thallium(I) carbonate, etc.), acetates (e.g., potassium acetate, cesium acetate, etc.), phosphates (e.g., tripotassium phosphate) hydroxides (e.g., potassium hydroxide, sodium hydroxide, etc.), ethoxides (e.g., sodium ethoxide, thallium(I) ethoxide, etc.), amines (e.g., triethylamine), basic fluoride salts (e.g., potassium fluoride, sodium fluoride, and cesium fluoride).

In certain embodiments, a suitable base may be provided in a stoichiometric amount. For example, in certain embodiments, the amount of the base is at least 1 molar equivalent, e.g., at least 1.5 molar equivalent, or at least 2 molar equivalent, or at least 2.5 molar equivalent, or at least 3 molar equivalent, based on the amount of the halopyrazolylthiazole.

In certain embodiments, the coupling of the halopyrazolylthiazole and the organoboron may be carried out in presence of Pd(dppf)Cl$_2$ and a carbonate (e.g., potassium carbonate).

Coupling of the pyrazolylthiazole and the organoboron as otherwise described herein can be carried out in a solvent in certain embodiments. Suitable solvents include, but are not limited to, dioxane, toluene, THF, DMF, dichloromethane, water, and combinations thereof. In certain embodiments, the solvent is water and one or more of dioxane, toluene, or DMF. In some embodiments, the ratio of water and one or more of dioxane, toluene, or DMF in the solvent is 2:1 to 1:5, for example, the ratio is 1:1 to 1:5, or 1:1 to 1:4, or 1:2 to 1:5, or 1:2 to 1:4, or 1:3 to 1:5, or 2:1 to 1:2, or 2:1 to 1:2.

In the methods of preparing the compound of formula (I), any organoboron bearing $R^5$ moiety well-suited for a Suzuki reaction may be used. For example, certain organoborons suitable for the methods of the disclosure include boronic acids and boronic esters having $R^5$ substituted on the boron, including those of formula:

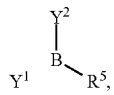

wherein
$R^5$ is as described for formula (I), and
$Y^1$ and $Y^2$ are independently hydroxy or $C_1$-$C_4$ alkoxy, or $Y^1$ and $Y^2$ together with the B atom form a 5-6 membered ring with one or two oxygens in the ring bound to the boron.

In certain embodiments, the organoboron is 2-$R^5$-4,4,5,5-tetramethyl-1,3,2-dioxaborolane, 2-$R^5$-boronic acid, 2-$R^5$-5,5-dimethyl-1,3,2-dioxaborinane, or 2-$R^5$-1,3,2-dioxaborinane. In certain embodiments, the organoboron is 2-$R^5$-4,4,5,5-tetramethyl-1,3,2-dioxaborolane.

The halopyrazolylthiazole and the organoboron may be coupled at a temperature and for a time sufficient to obtain the compound of formula (I).

For example, in certain embodiments, the pyrazolylthiazole and the organoboron are coupled at a temperature of at least 80° C., e.g., at least 85° C., or at least 90° C., or at least 95° C., or at least 100° C., or at least 110° C. In certain embodiments, the halopyrazolylthiazole and the organoboron are coupled at a temperature in a range of 80° C. to 120° C., for example, in a range of 80° C. to 110° C., or 80° C. to 100° C., or 80° C. to 90° C., or 90° C. to 120° C., or 90° C. to 110° C., or 90° C. to 100° C., or 100° C. to 120° C., or 100° C. to 110° C.

In certain embodiments, the halopyrazolylthiazole and the organoboron may be coupled for at least 8 hours. For example, in various embodiments, the halopyrazolylthiazole and the organoboron are coupled for at least 10 hours, e.g., at least 12 hours, or at least 14 hours, or at least 16 hours. In another embodiment, the halopyrazolylthiazole and the organoboron are coupled for a time in a range of 8 hours to 24 hours. For example, in various embodiments the halopyrazolylthiazole and the organoboron may be coupled for a time in range of 8 hours to 20 hours, or 8 hours to 16 hours, or 8 hours to 14 hours, or 8 hours to 12 hours, or 8 hours to 10 hours, or 10 hours to 24 hours, or 10 hours to 20 hours, or 10 hours to 16 hours, or 10 hours to 14 hours, or 10 hours to 12 hours, or 14 hours to 24 hours, or 14 hours to 20 hours, or 14 hours to 18 hours, or 14 hours to 16 hours, or 16 hours to 24 hours, or 16 hours to 20 hours, or 16 hours to 18 hours, or 18 hours to 24 hours, or 18 hours to 20 hours.

In certain embodiments of the methods as described herein, a desired compound of formula (I) is one in which Q is —C(O)OH, e.g., of formula:

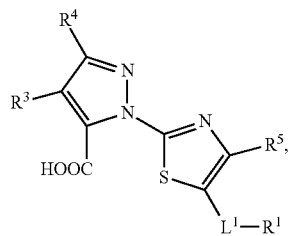

or a pharmaceutically acceptable salt thereof. Such methods can further comprise converting the coupling reaction product to the corresponding carboxylic acid, for example by hydrolysis (e.g., hydrolyzing a compound of formula (I) in which $Q^1$ is —C(O)OR$^{2C}$, and R$^{2C}$ is $C_1$-$C_3$ alkyl or a protecting group). In certain embodiments, the methods as described herein further comprise hydrolyzing the compound of formula (I) wherein $Q^1$ is —C(O)O($C_1$-$C_3$ alkyl) to provide the corresponding carboxylic acid or carboxylate.

In certain embodiments, the methods as described herein further comprise hydrolyzing the compound of formula (I) wherein $Q^1$ is —C(O)O($C_1$-$C_3$ alkyl) to obtain a carboxylate salt of the compound of formula (I); and crystalizing the salt of the compound of formula (I).

The method can further include converting the salt to the corresponding carboxylic acid. In certain embodiments, the salt is treated with an acid to obtain the carboxylic acid compound of formula (I). In certain embodiments of this method, the compound of formula (I) is obtained with purity of at least 98%.

Certain embodiments of the methods as otherwise described herein are where the compounds have any of the structural formulae (I)—(Ib) above, for example, structural formula (I), (Ia), or (Ib), in which the variables are as otherwise described in any embodiment herein, and $R^1$ is optionally substituted $C_1$-$C_8$ alkyl. In certain embodiments, $R^1$ is unsubstituted $C_1$-$C_8$ alkyl or fluorinated $C_1$-$C_8$ alkyl. In certain embodiments, $R^1$ is unsubstituted $C_1$-$C_8$ alkyl. In certain embodiments, $R^1$ is optionally substituted $C_1$-$C_5$ alkyl. In certain embodiments, $R^1$ is unsubstituted $C_1$-$C_5$ alkyl or fluorinated $C_1$-$C_5$ alkyl. In certain embodiments, $R^1$ is unsubstituted $C_1$-$C_5$ alkyl. In certain embodiments, $R^1$ is optionally substituted $C_2$-$C_5$ alkyl. In certain embodiments, $R^1$ is unsubstituted $C_1$-$C_8$ alkyl or fluorinated $C_2$-$C_5$ alkyl. In certain embodiments, $R^1$ is unsubstituted $C_2$-$C_5$ alkyl. In certain embodiments, $R^1$ is hydroxymethyl, methoxymethyl, hydroxyethyl or methoxyethyl. In certain embodiments, $R^1$ is methyl, ethyl, propyl, isopropyl, butyl, or tert-butyl. In certain embodiments, $R^1$ is propyl, isopropyl, butyl, or tert-butyl. In certain embodiments, $R^1$ is isopropyl.

Other embodiments of the methods as otherwise described herein are where the compounds have any of the structural formulae (I)—(Ib) above, in which the variables are as otherwise described in any embodiment herein, and $L^1$ is a bond, —O—, —S—, —S(O)—, or —S(O)—. In certain embodiments, $L^1$ is —O—, —S—, —S(O)—, or —S(O)$_2$—. In certain embodiments, $L^1$ is —S—, —S(O)—, or —S(O)$_2$—. In certain embodiments, L$^1$ is —S—. In certain embodiments, L$^1$ is a bond. In certain embodiments, L$^1$ is —O—, or wherein L$^1$ is —NR$^6$—.

Other embodiments of the methods as otherwise described herein are where the compounds have any of the structural formulae (I)—(Ib) above, in which the variables are as otherwise described in any embodiment herein, and R$^3$ is phenyl or heteroaryl (each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^E$. In certain embodiments, R$^3$ is phenyl (i) substituted with a single substituent selected from -L$^{3C}$-(phenyl optionally substituted with 1-5 R$^{3Q}$), -L$^{3C}$-(heteroaryl optionally substituted with 1-5 R$^3$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^E$. In certain embodiments, R$^3$ is phenyl (i) substituted with a single substituent selected from -L$^{3C}$-(phenyl optionally substituted with 1-5 R$^3$), -L$^{3C}$-(heteroaryl optionally substituted with 1-5 R$^{3D}$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^E$. In certain embodiments, R$^3$ is heteroaryl (e.g., an isothiazole, a pyridone, a thiadiazole, a pyrazine, an imidazole, a benzofuran, an indole, a pyridine, a pyrazole, an isoxazole, a thiophene, a furan or a pyrimidine) (i) substituted with a single substituent selected from -L$^{3C}$-(phenyl optionally substituted with 1-5 R$^{3D}$), -L$^{3C}$-(heteroaryl optionally substituted with 1-5 R$^D$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^{3E}$. In certain embodiments, R$^3$ is heteroaryl (e.g., an isothiazole, a pyridone, a thiadiazole, a pyrazine, an imidazole, a benzofuran, an indole, a pyridine, a pyrazole, an isoxazole, a thiophene, a furan or a pyrimidine) (i) substituted with a single substituent selected from -L$^{3C}$-(phenyl optionally substituted with 1-5 R$^{3D}$), -L$^{3C}$-(monocyclic heteroaryl optionally substituted with 1-5 R$^{3D}$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^{3E}$. In certain embodiments, R$^3$ is selected from the group consisting of: phenyl, imidazolyl, oxazolyl, isoxazolyl, isothiazolyl, thiazolyl, pyridinyl, pyrazinyl, pyridonyl, thiadiazolyl, pyrazolyl, triazolopyridinyl, thienyl, furanyl and pyrimidinyl, each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^{3E}$.

In certain other embodiments of the methods as otherwise described herein, the compounds have any of the structural formulae (I)—(Ia) above, in which the variables are as otherwise described in any embodiment herein, and R$^3$ is phenyl optionally substituted with 1-5 R$^{3E}$. In certain embodiments, R$^3$ is phenyl optionally substituted with 1-2 R$^{3E}$. In certain embodiments, R$^3$ is phenyl optionally substituted with R$^{3E}$. In certain embodiments, R$^3$ is phenyl substituted with 1-2 R$^{3E}$. In certain embodiments, R$^3$ is phenyl substituted with R$^{3E}$. In certain embodiments, R$^3$ is heteroaryl (e.g., an isothiazole, a pyridone, a thiadiazole, a pyrazine, an imidazole, a benzofuran, an indole, a pyridine, a pyrazole, an isoxazole, a thiophene, a furan or a pyrimidine) optionally substituted with 1-5 R$^{3E}$. In certain embodiments, R$^3$ is selected from the group consisting of phenyl and heteroaryl (e.g., pyridyl, pyrazolyl), optionally substituted with 1-5 R$^E$. In certain embodiments, R$^3$ is phenyl substituted with a halogen. In certain embodiments, R$^3$ is 3-fluorophenyl.

Other embodiments of the methods as otherwise described herein are where the compounds have any of the structural formulae (I)—(Ia) above, in which the variables are as otherwise described in any embodiment herein, and each R$^{3E}$ is independently selected from C$_1$-C$_4$ alkyl, C$_1$-C$_4$ fluoroalkyl, halogen, —OR$^{3F}$, and —NR$^{3G}$R$^{3F}$. In certain embodiments, each R$^{3E}$ is independently selected from halogen, —OR$^{3F}$, and —NR$^{3G}$R$^{3F}$. In certain embodiments, each R$^{3E}$ is independently selected from C$_1$-C$_4$ alkyl, C$_1$-C$_4$ fluoroalkyl, and halogen. In certain embodiments, each R$^{3E}$ is independently selected from C$_1$-C$_4$ alkyl, halogen, —OR$^{3F}$, and —NR$^{3G}$R$^{3F}$. In certain embodiments, each R$^{3E}$ is independently selected from C$_1$-C$_4$ fluoroalkyl and halogen. In certain embodiments, each R$^4$ is independently halogen.

Certain embodiments of the methods as otherwise described herein are where the compounds have any of the structural formulae (I)—(Ia) above, in which the variables are as otherwise described in any embodiment herein, and R$^4$ is optionally substituted C$_1$-C$_8$ alkyl, optionally-substituted C$_1$-C$_8$ alkenyl or optionally substituted C$_1$-C$_8$ alkynyl. In certain embodiments, R$^4$ is optionally substituted C$_1$-C$_8$ alkyl. In certain embodiments, R$^4$ is hydrogen or unsubstituted C$_1$-C$_6$ alkyl. In certain embodiments, R$^4$ is unsubstituted C$_1$-C$_3$ alkyl. In certain embodiments, R$^4$ is unsubstituted methyl.

Certain embodiments of the methods as otherwise described herein are where the compounds have any of the structural formula (I) above, in which the variables are as otherwise described in any embodiment herein, and R$^5$ is phenyl or heteroaryl (e.g., an isoxazoyl, a pyridyl, a pyrazolyl), each optionally substituted with 1-5 R$^{5E}$. In certain embodiments, R$^5$ is heterocycloalkyl optionally substituted with 1-5 R$^{5E}$. In certain embodiments, R$^5$ is cycloalkyl optionally substituted with 1-5 R$^{5E}$. In certain embodiments, R$^5$ is cycloalkyl is substituted with 1-5 R$^{SE}$. In certain embodiments, R$^5$ is unsaturated cycloalkyl optionally substituted with 1-5 R$^{5E}$. In certain embodiments, R$^5$ is unsaturated cycloalkyl substituted with 1-5 R$^{5E}$. In certain embodiments, R$^5$ is cyclohexenyl substituted with R$^{5E}$. In certain embodiments, R$^5$ is 4-(trifluoromethyl)cyclohex-1-en-1-yl.

Certain embodiments of the methods as otherwise described herein are where the compounds have any of the structural formula (I) above, in which the variables are as otherwise described in any embodiment herein, and Q is —C(O)OR$^{2A}$ or —C(O)NR$^2$R$^{2A}$. In certain embodiments, Q is —C(O)OR$^{2A}$. In certain embodiments, Q is —C(O)OH or —C(O)O(C$_1$-C$_3$ alkyl). In certain embodiments, Q is —C(O)OH.

In certain embodiments of the methods of the disclosure, the compound of formula (I) is: 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid, optionally in the form of a pharmaceutically acceptable salt, and/or a solvate or hydrate.

In certain embodiments of the methods of the disclosure, the compound of formula (I) is: C$_1$-C$_3$ alkyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally in the form of a solvate or hydrate. In certain embodiments of the methods of the disclosure, the compound of formula (I) is: ethyl 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylate, optionally in the form of a solvate or hydrate.

Certain embodiments of the methods as otherwise described herein are where the compounds have any of the structural formula (Ia) above, in which the variables are as otherwise described in any embodiment herein, and $Q^1$ is —C(O)OR$^{2C}$ or —C(O)NR$^{2B}$R$^{2C}$. In certain embodiments, $Q^1$ is —C(O)OR$^{2C}$. In certain embodiments, $Q^1$ is —C(O)O(C$_1$-C$_3$ alkyl). In certain embodiments, $Q^1$ is —C(O)O(ethyl). In certain embodiments, $Q^1$ is —C(O)OR$^{2C}$ and R$^{2C}$ is a protecting group.

In certain embodiments of the methods of the disclosure, the compound of formula (Ia) is:

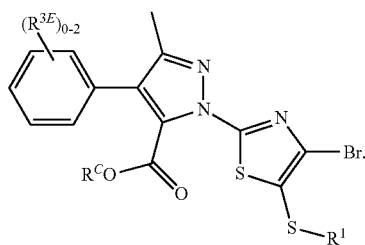

In certain embodiments of the methods of the disclosure, the compound of formula (Ia) is:

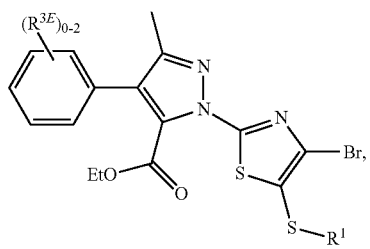

wherein $R^1$ is $C_1$-$C_8$ alkyl, and $R^{3E}$ is independently selected from $C_1$-$C_4$ alkyl, $C_1$-$C_4$ fluoroalkyl, halogen, —OR$^{3F}$, and —NR$^{3G}$R$^{3F}$.

In certain embodiments of the methods of the disclosure, the pyrazolylthiazole of formula (Ia) is $C_1$-$C_3$ alkyl 1-(4-halo-5-(isopropylthio)thiazol-2-yl)-4-(3-fluorophenyl)-3-methyl-1H-pyrazole-5-carboxylate. In certain embodiments of the methods of the disclosure, the pyrazolylthiazole of formula (Ia) is ethyl 1-(4-bromo-5-(isopropylthio)thiazol-2-yl)-4-(3-fluorophenyl)-3-methyl-1H-pyrazole-5-carboxylate.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" with reference to the chemical structure referred to unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. CH$_3$—CH$_2$—), in some circumstances a bivalent linking moiety can be "alkyl," in which case those skilled in the art will understand the alkyl to be a divalent radical (e.g., —CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium sat. On occasion a moiety may be defined, for example, as —B-(A)$_a$, wherein a is 0 or 1. In such instances, when a is 0 the moiety is —B and when a is 1 the moiety is —B-A.

As used herein, the term "alkyl" includes a saturated hydrocarbon having a designed number of carbon atoms, such as 1 to 10 carbons (i.e., inclusive of 1 and 10), 1 to 8 carbons, 1 to 6 carbons, 1 to 3 carbons, or 1, 2, 3, 4, 5 or 6. Alkyl group may be straight or branched and depending on context, may be a monovalent radical or a divalent radical (i.e., an alkylene group). For example, the moiety "—(C$_1$-C$_6$alkyl)-O—" signifies connection of an oxygen through an alkylene bridge having from 1 to 6 carbons and C$_1$-C$_3$alkyl represents methyl, ethyl, and propyl moieties. Examples of "alkyl" include, for example, methyl, ethyl, propyl, isopropyl, butyl, iso-, sec- and tert-butyl, pentyl, and hexyl.

The term "alkoxy" represents an alkyl group of indicated number of carbon atoms attached to the parent molecular moiety through an oxygen bridge. Examples of "alkoxy" include, for example, methoxy, ethoxy, propoxy, and isopropoxy.

The term "alkenyl" as used herein, unsaturated hydrocarbon containing from 2 to 10 carbons (i.e., inclusive of 2 and 10), 2 to 8 carbons, 2 to 6 carbons, or 2, 3, 4, 5 or 6, unless otherwise specified, and containing at least one carbon-carbon double bond. Alkenyl group may be straight or branched and depending on context, may be a monovalent radical or a divalent radical (i.e., an alkenylene group). For example, the moiety "—(C$_1$-C$_6$ alkenyl)-O—" signifies connection of an oxygen through an alkenylene bridge having from 2 to 6 carbons. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkynyl" as used herein, unsaturated hydrocarbon containing from 2 to 10 carbons (i.e., inclusive of 2 and 10), 2 to 8 carbons, 2 to 6 carbons, or 2, 3, 4, 5 or 6 unless otherwise specified, and containing at least one carbon-carbon triple bond. Alkynyl group may be straight or branched and depending on context, may be a monovalent radical or a divalent radical (i.e., an alkynylene group). For example, the moiety "—(C$_1$-C$_6$ alkynyl)-O—" signifies connection of an oxygen through an alkynylene bridge having from 2 to 6 carbons. Representative examples of alkynyl include, but are not limited to, acetylenyl, 1-propynyl, 2-propynyl, 3-butynyl, 2-pentynyl, and 1-butynyl.

The terms "halogen" or "halo" indicate fluorine, chlorine, bromine, and iodine. In certain embodiments of each and every embodiment as otherwise described herein, the term "halogen" or "halo" refers to fluorine, chlorine, or bromine. The term "fluoroalkyl" indicates an alkyl group (i.e., as otherwise described herein) that is substituted with at least one fluorine. "Fluoroalkyl" includes alkyl groups substituted with multiple fluorines, such as perfluoroalkyl groups. Examples of fluoroalkyl groups include fluoromethyl, difluoromethyl, trifluoromethyl, pentafluoroethyl, 2,2,2-trifluoroethyl, 1,1,1,3,3,3-hexafluoroprop-2-yl and 2,2,3,3,3-pentafluoroprop-1-yl.

The term "heteroaryl" refers to an aromatic ring system containing at least one aromatic heteroatom selected from nitrogen, oxygen and sulfur in an aromatic ring. Most commonly, the heteroaryl groups will have 1, 2 or 3 heteroatoms. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom.

The term "heterocycloalkyl" refers to a non-aromatic ring containing at least one heteroatom that is preferably selected from nitrogen, oxygen and sulfur, wherein said heteroatom is in a non-aromatic ring. The heterocycloalkyl may have 1, 2 or 3 heteroatoms. The heterocycloalkyl may be saturated (i.e., a heterocycloalkyl) or partially unsaturated (i.e., a heterocycloalkenyl). In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, morpholinyl, thiomorpholinyl, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, homopiperidinyl, homomorpholinyl, homothiomorpholinyl, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, and tetrahydrothienyl. Especially desirable heterocycloalkyl groups include morpholinyl, tetrahydropyranyl, piperidinyl, pyrrolidinyl, piperazinyl, azepanyl, azetidinyl, thiomorpholinyl, 2-oxazolidonyl, imidazolidonyl, and piperazinonyl.

The term "cycloalkyl" refers to a non-aromatic carbocyclic ring or ring system, which may be saturated (i.e., a cycloalkyl) or partially unsaturated (i.e., a cycloalkenyl). Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclohexenyl, cyclopentyl, cyclobutyl, and cyclopropyl. The cycloalkyl groups herein are unsubstituted or, when specified as "optionally substituted", may be substituted in one or more substitutable positions with various groups, as indicated.

The term "oxo" means a doubly bonded oxygen, sometimes designated as =O or for example in describing a carbonyl "C(O)" may be used to show an oxo substituted carbon.

The term "substituted," when used to modify a specified group or radical, means that one or more hydrogen atoms of the specified group or radical are each, independently of one another, replaced with the same or different substituent groups as defined below, unless specified otherwise.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

A "leaving group" (e.g., suitable as X), as used herein refers to a moiety of a reactant (e.g., the alkylhalogenide of the disclosure) reaction that is displaced from the first reactant in the chemical reaction. A comprehensive list of suitable leaving groups can be found in J. March, *Advanced Organic Chemistry*, John Wiley and Sons, N.Y. (2013). Examples of suitable leaving groups include, but are not limited to, halogen (such as Cl or Br), acetoxy, and sulfonyloxy groups (such as methyl sulfonyloxy, trifluoromethylsulfonyloxy ("triflate"), p-toluenesulfonyloxy ("tosylate")).

A "protecting group" (e.g., suitable as $R^{2A}$ or $R^{2C}$), as used herein refers to those groups that are stable to the conditions of subsequent reaction(s) at other positions of the molecule, which may be removed at the appropriate point without disrupting the remainder of the molecule, to give the unprotected Q or $Q^1$. The suitable protecting group may be selected depending on the nature of the group to be protected (e.g., Q or $Q^1$) and the conditions used in the methods of the disclosure. A comprehensive list of suitable protective groups can be found in T. W. Greene, *Protective Groups in Organic Synthesis*, John Wiley & Sons, Inc. (1999), the disclosure of which is incorporated herein by reference in its entirety. For example, carboxylic acid moiety may be protected in form of ester having an alkyl or substituted alkyl group (e.g., methyl, ethyl, tertbutyl allyl, triphenylmethyl (trityl), etc.) or an ester having an arylalkyl or substituted arylalkyl group (e.g., benzyls, such as 4-nitrobenzyl, 4-methoxybenzyl, 3,4-dimethoxybenzyl, etc.), in form of a thioester (e.g., tertbutyl thioester), in form of a silyl esters (e.g., trimethylsilyl, tertbutydimethyisilyl), and the like. An amide moiety may be protected in form of carbamate having an alkyl or substituted alkyl group (e.g., tertbutyl carbamate).

EXAMPLES

The methods of the disclosure are illustrated further by the following examples, which are not to be construed as limiting the disclosure in scope or spirit to the specific procedures and reagents described in them.

Example 1: Preparation of 4-bromo-2-hydrazinyl-5-(isopropylthio)thiazole (Compound 4)

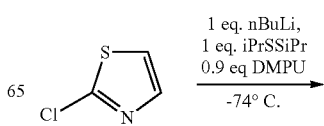

-continued

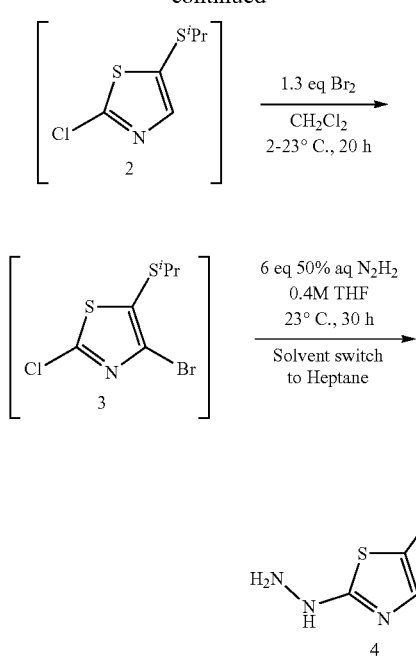

To a dry round bottom flask was added 2-chloro thiazole (51 g, 0.43 mol), N,N'-dimethylpropyleneurea (45.5 mL, 0.378 mol) and anhydrous tetrahydrofuran (1.0 L) under nitrogen. The clear, colorless solution was cooled in a dry ice-acetone bath to −74° C. and then a hexane solution of n-butyl lithium (262 mL, 0.43 mol) was added dropwise over 120 min while keeping the temperature <−72 C°. The brown solution was stirred for 30 min, then a solution of di-isopropyl disulfide (61.6 g, 0.410 mol) in anhydrous tetrahydrofuran (200 mL) was added over 120 min and the mixture allowed to stir an additional 30 min at <−72 C°. The reaction mixture was then transferred over 70 min via cannula to a 5 L flask containing 3 N HCl (1 L) cooled to 1° C. The resulting biphasic mixture was stirred an additional 30 min and then extracted with heptanes (1×1 L, 1×500 mL) and washed with brine (100 mL).

The solvent was removed under reduced pressure and the resulting oil dissolved in dichloromethane (850 mL). The resulting solution was cooled in an ice bath to 2° C. and a solution of bromine (86.8 g, 0.543 mmol) in heptanes (100 mL) was added dropwise over 60 min and the solution stirred for 1 h then allowed to warm to room temperature (20-22° C.) over 18 h. Sodium thiosulfate (30 g) in water (500 mL) was then added and let stir for 1 h. The aqueous phase was extracted with dichloromethane (200 mL) and the combined organic phases washed with brine (100 mL) and the solvent removed under reduced pressure.

This oil was then dissolved in tetrahydrofuran (1.0 L) and 50% hydrazine in water (150 mL, 2.5 mol) added. The biphasic mixture was stirred at room temperature (20-23° C.) for 30 h. The organic layer was then concentrated to 175 mL and heptanes (250 mL) added dropwise over 20 min. Seed crystals of the title compound (10 mg) were added and the mixture agitated for 1 h. Heptanes (250 mL) were then added, resulting in rapid crystallization. The mixture was cooled to 5° C., filtered, and washed with heptanes (2×250 mL). The filtrate was concentrated under reduced pressure to 700 mL, cooled to 2° C. overnight, and filtered, washing with heptanes (2×100 mL). The combined solids from the filtration steps were dried in air to obtain the title compound (79.5 g, 72%) as a light beige solid. $^1$H NMR (500 MHz, CDCl$_3$) δ 8.66 (br, 1H), 4.16 (br, 2H), 3.17 (m, 1H), 1.28 (s, 6H). $^{13}$C NMR (500 MHz, CDCl$_6$) δ 176.48, 130.48, 111.51, 41.44, 23.06. MS (m/z): 268 [M+1]$^+$.

Example 2: Recrystallization of Compound 4

A 12 L flask was charged with compound 4 (186.6 g, 0.6957 mol) and isopropyl alcohol (2 L). The slurry was warmed to 65° C. and water (2 L) added to form a homogeneous solution. The contents were allowed to cool to 35° C. and additional water (500 mL) added dropwise over 30 min, whereupon crystallization ensued. The mixture was stirred for 1 h then water (1.5 L) added over 1.5 h. The resulting slurry was stirred overnight and then cooled to 10° C. The mixture was filtered, washed with cold (5° C.) isopropanol:water (1:2) (3×500 mL) and dried overnight to give the title compound as a light beige solid (166.2 g, 90.2%).

Example 3: Preparation No. 1 of ethyl 2-(4-bromo-5-isopropylsulfanyl-thiazol-2-yl)-4-(3-fluorophenyl)-5-methyl-pyrazole-3-carboxylate (Compound 8)

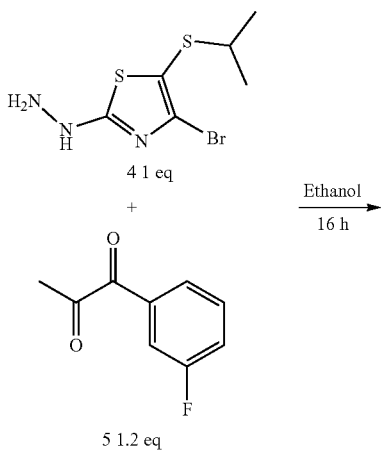

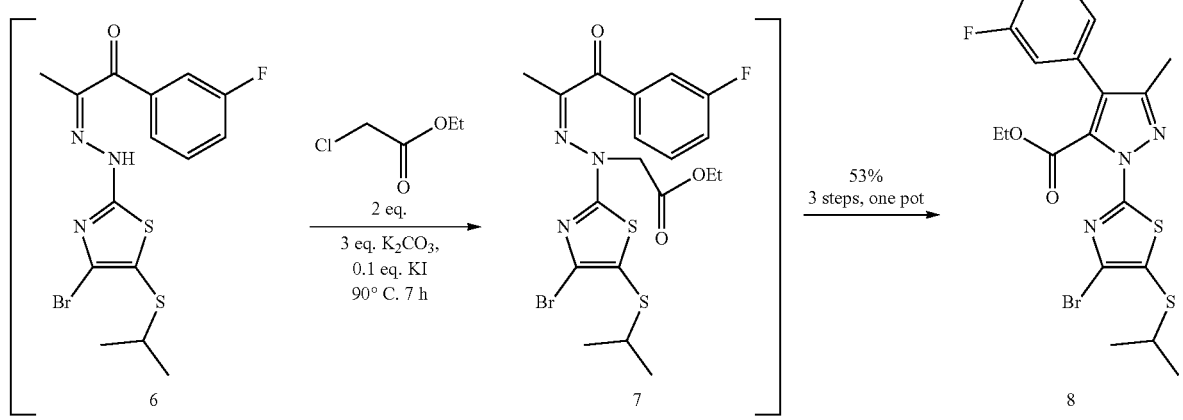

A solution of compound 4 (6.21 g, 23.2 mmol) and 1-(3-fluorophenyl)propane-1,2-dione (5 g, 30.1 mmol) in ethanol (140 mL) was stirred for 16 h. The reaction was then charged with ethyl 2-chloroacetate (11.35 g, 92.6 mmol), potassium carbonate (19.2 g, 139 mmol), and potassium iodide (3.84 g, 23.2 mmol). The reaction turned red-brown and was heated to 90° C. for 7 h under reflux. The reaction was then cooled to 20-25° C., heptane added (40 mL), and the reaction concentration to 60 mL. The mixture was then charged with aqueous sodium thiosulfate (300 mL) and extracted with heptane (3×150 mL). The yellow organic layers were combined, dried with sodium sulfate, filtered, and concentrated to a viscous orange solution that solidified upon addition of alcohol (10 mL). The mixture was cooled to 0-5° C., let stand 1 h, then filtered. The filtered solid was washed with alcohol (3×5 mL) and dried under vacuum at 30° C. to generate the title compound (5.9 g, 53%).

Example 4: Preparation No. 2 of Compound 8

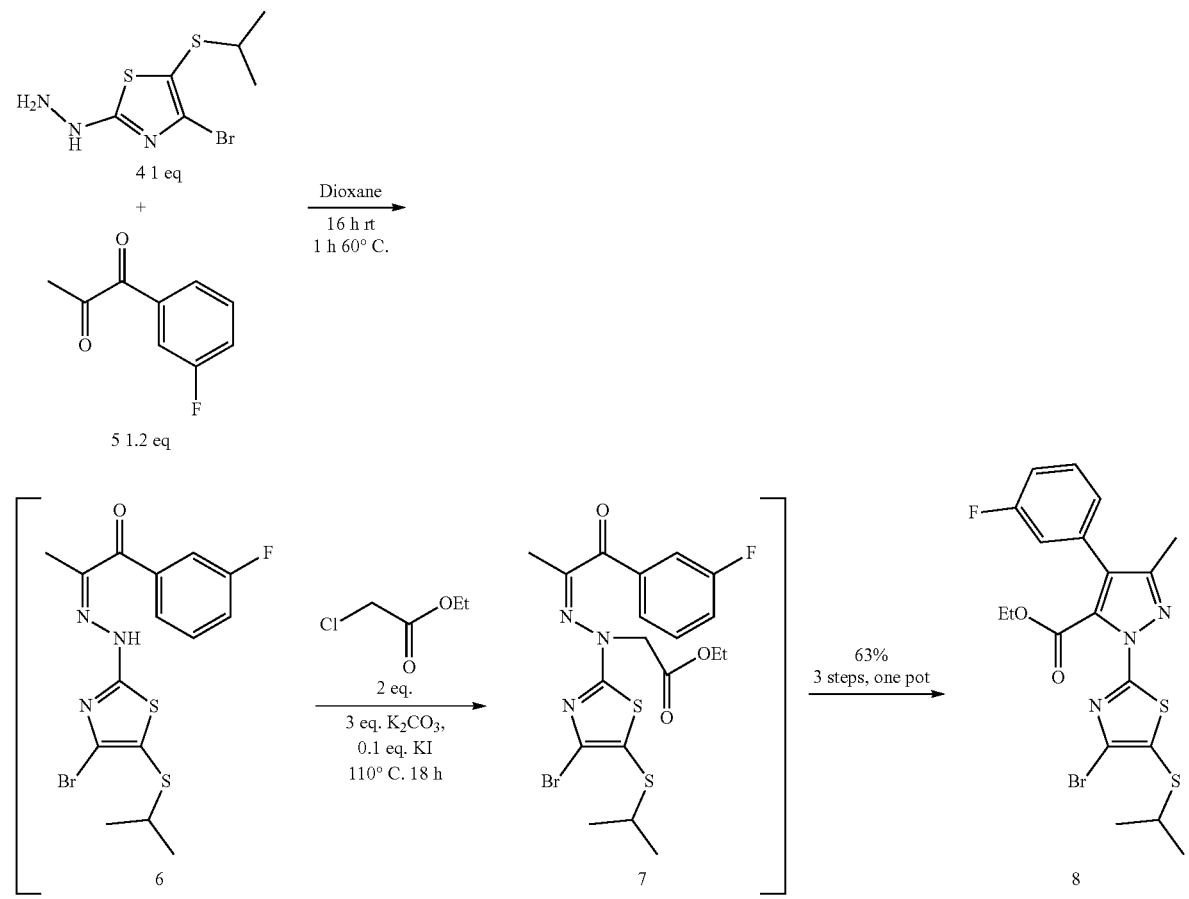

A solution of compound 4 (2.36 g, 8.8 mmol) in dioxane (53 mL) was charged with 1-(3-fluorophenyl)propane-1,2-dione (2.19 g, 13.2 mmol) and stirred at room temperature for 16 h then heated to 60° C. for 1 h. The reaction was then cooled and charged sequentially with ethyl 2-chloroacetate (2.16 g, 17.6 mmol), potassium carbonate (7.30 g, 52.8 mmol), and potassium iodide (146.1 mg, 0.8800 mmol) and heated to 110° C. for 18 h. The reaction was cooled to room temperature, heptane (100 mL) added, and then concentrated under reduced pressure to 150 mL. Water (100 mL) was then added and the mixture extracted with heptane (3×100 mL). The combined organic layers were concentrated to 20 mL and filtered through a silica gel pad with 10% ethyl acetate in heptane as eluent. The solvent was removed from the resulting yellow solution and crystallized with ethanol (10 mL). The mixture was then cooled to 0° C. and filtered, washing with cold ethanol (2×3 mL) and dried at 35° C. under reduced pressure to provide the title compound (2.67 g, 63%). $^1$H NMR (500 MHz, CDCl$_3$) δ 7.4 (m, 1H), 7.2 (d, 1H), 7.1 (m, 1H), 4.35 (q, 2H), 3.3 (quint, 1H), 2.35 (s, 3H), 1.35 (s, 6H), 1.30 (t, 3H). $^{13}$C{$^1$H} NMR (500 MHz, CDCl$_6$) δ 163.65, 161.69, 160.73, 160.27, 150.80, 132.16, 131.22, 130.19, 125.06, 124.04, 123.13, 116.35, 115.00, 62.79, 41.85, 23.03, 13.83, 12.63. $^{19}$F NMR (500 MHz, CDCl$_6$) δ −112.55−−112.47 (quint). MS (m/z): 485.65 [M+1]$^+$.

Example 5: Preparation of ethyl 4-(3-fluorophenyl)-2-[5-isopropylsulfanyl-4-[4-(trifluoromethyl)cyclohexen-1-yl]thiazol-2-yl]-5-methyl-pyrazole-3-carboxylate (Compound 10)

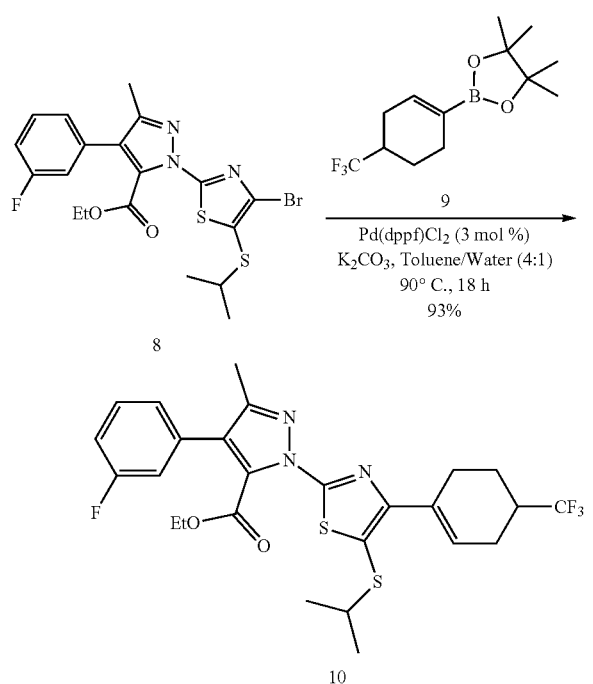

A 1 L flask was charged with 4,4,5,5,-tetramethyl-2-[4-(trifluoromethyl)cyclohexen-1-yl]-1,3,2-dioxaborolane (21.39 g, 77.49 mmol), compound 8 (31.28 g, 64.57 mmol), Pd(dppf)Cl$_2$·CH$_2$Cl$_2$ (1.58 g, 1.94 mmol) and potassium carbonate (26.77 g, 193.7 mmol). Degassed toluene (360 mL) and deionized water (90 mL) were added to the flask and the mixture was heated to 90° C. over the course of 1 h. After 18 h, the reaction mixture was cooled to room temperature and filtered through celite and washed with ethyl acetate (50 mL). The organic layer was separated and dried over sodium sulfate and charged with silica gel (150 g). The resulting slurry was evaporated to dryness, poured onto a pad of silica and eluted with 5% ethyl acetate in heptanes (1 L). Evaporation of the organic solvents and standing overnight gave the title compound (36.62 g, 93.4% yield). $^1$H NMR (500 MHz, CDCl$_6$) δ 7.35 (m, 1H), 7.15 (d, 1H), 7.05 (m, 1H), 6.30 (s, 1H), 4.25 (q, 2H), 3.15 (quint, 1H), 2.70 (d, 1H), 2.40 (m, 2H), 2.25 (s, 3H), 2.05 (d, 1H), 1.50-1.60 (m, 3H), 1.20-1.25 (m, 6H), 1.10-1.15 (t, 3H). $^{13}$C{$^1$H} NMR (500 MHz, CDCl$_3$) δ 161.23, 159.77, 159.16, 156.09, 153.41, 148.05, 137.15, 130.63, 130.50, 129.52, 127.20, 126.10, 123.12, 118.87, 114.47, 113.11, 60.39, 40.62, 36.46, 25.13, 21.61, 20.80, 19.77, 11.85, 10.66. $^{19}$F NMR (500 MHz, CDCl$_6$) δ−73.68, −112.72. MS (m/z): 553.90 [M+1]$^+$.

Example 6: Preparation of sodium 4-(3-fluorophenyl)-2-[5-isopropylsulfanyl-4-[4-(trifluoromethyl)cyclohexen-1-yl]thiazol-2-yl]-5-methyl-pyrazole-3-carboxylate (Compound 11)

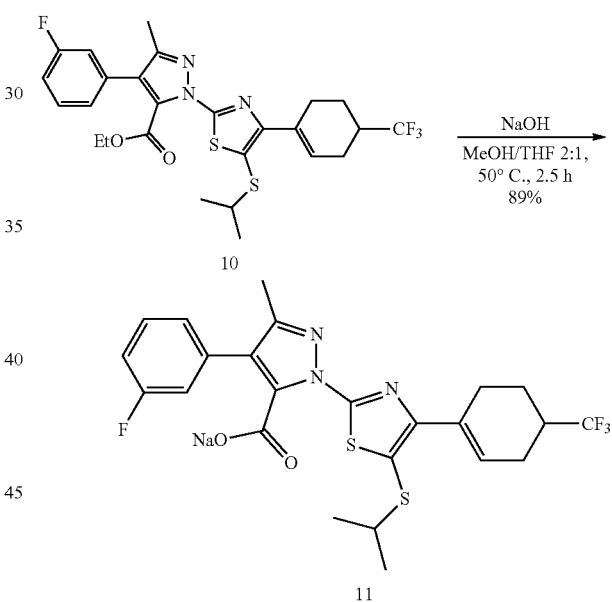

To a solution of methanol (150 mL), tetrahydrofuran (75 mL) was added compound 10 (17.83 g, 28.79 mmol). Aqueous sodium hydroxide (1.0 N, 64 mL) was added and the resulting slurry heated to 50° C. for 2.5 h. Evaporation under reduced pressure gave a beige solid which was agitated with deionized water (3×500 mL) and filtered. The solid was allowed to dry under reduced pressure until constant weight and then was suspended in acetonitrile (100 mL). After 15 min the mixture was filtered to give the title compound (14.00 g, 89%). $^1$H NMR (500 MHz, DMSO-d$_6$) δ 7.40-7.50 (m, 1H), 7.35 (t, 2H), 7.10 (t, 2H), 6.40 (s, 1H), 3.25 (quint, 1H), 2.25 (d, 1H), 2.55 (br, 1H), 2.45 (s, 3H), 2.25 (s, 3H), 2.10 (d, 1H), 1.55 (m, 1H), 1.23 (s, 6H). $^{13}$C{$^1$H} NMR (500 MHz, DMSO-d$_6$) δ 163.49, 162.98, 161.56, 158.98, 155.35, 149.20, 143.75, 135.74, 131.92, 130.32, 127.41, 125.02, 118.26, 115.68, 113.44, 42.29, 37.34, 26.85, 24.60, 23.18, 21.75, 13.42. $^{19}$F NMR (500 MHz, DMSO-d$_6$) δ −72.06 (s), −113.60 (quint). MS (m/z): 525.85 [M-Na+2]$^+$.

Example 7: Recrystallization of Compound 11

Compound 11 was then recrystallized. 56 g (0.10 mol) of compound 11 was dissolved in tetrahydrofuran (500 mL) and filtered. To this solution was added acetonitrile (250 mL) and the solution concentrated to 350 mL at 50° C. under reduced pressure. Acetonitrile (250 mL) was added again and the resulting solution concentrated to 300 mL at 50° C. under reduced pressure, resulting in crystallization. To this mixture acetonitrile (250 ml) was added and again concentrated to 500 mL at 50° C. under reduced pressure. The mixture was then allowed to stand 1 h at 50° C., then cooled to 20° C. for 1 h, then cooled to 0° C. for 30 min. The resulting mixture was filtered and the solid washed with cold acetonitrile (2×100 mL, 0° C.) and dried at 35° C. under reduced pressure to provice compound 11 (54.7 g, 98%). MS (m/z): 525.85 [M-Na+2]$^+$. $^1$H NMR (500 MHz, DMSO-d$^6$) δ 14.16 (br s, 1H), 7.50-7.55 (m, 1H), 7.23-7.31 (m, 3H), 6.44 (m, 1H), 3.32 (m, 1H), 2.68-2.74 (m, 1H), 2.55-2.64 (m, 1H), 2.43-2.55 (m, 1H), 2.30 (s, 3H), 2.20-2.30 (m, 1H), 2.02-2.09 (m, 1H), 1.50-1.60 (m, 1H), 1.26 (d, 6H, J=7.5 Hz). $^{13}$C NMR (126 MHz, DMSO-d$^6$) δ 163.51, 162.37, 161.58, 157.70, 154.94, 150.62, 133.49, 132.86, 132.79, 131.44, 131.23, 131.16, 129.80, 127.98, 127.59, 125.55, 125.52, 125.38, 122.20, 120.09, 116.14, 115.96, 115.35, 115.19, 42.50, 26.71, 24.56, 23.15, 23.07, 21.64, 12.76.

Example 8: Preparation of 4-(3-fluorophenyl)-2-[5-isopropylsulfanyl-4-[4-(trifluoromethyl)-cyclohexen-1-yl]thiazol-2-yl]-5-methyl-pyrazole-3-carboxylic acid (Compound 1)

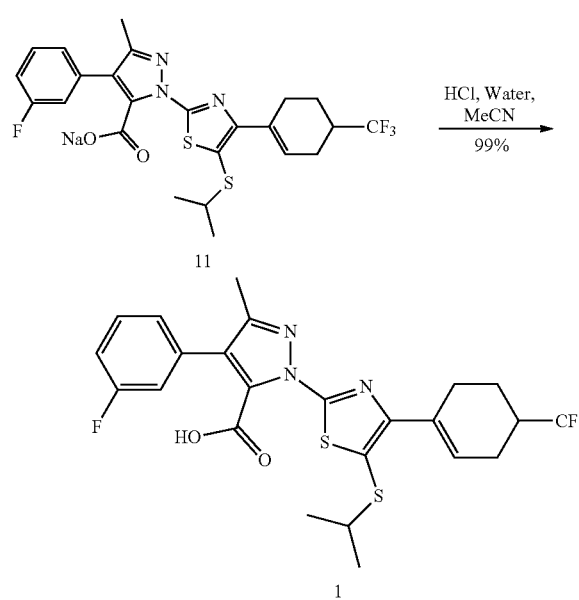

A 5 L flask was charged with compound 11 (52.0 g, 94.9 mmol) and 10% acetonitrile in dionized water (1.0 L). The mixture was stirred for 30 min and then warmed to 50° C. A seed of the title compound was added (1.2 g) and then 0.1N HCl (1.0 L) was added dropwise over 3.75 h. As the addition progressed a change in the slurry was noted as it became thicker. It was also observed that each drop of acid created a yellow color which dissipated with stirring. After 900 mL of acid was added the pH of the supernatant was monitored. As the addition approached 1.0 equivalents the pH dropped to about 3, the target pH being <4 to ensure complete protonation.

A sample was taken for analysis assay (XRPD, HPLC), the sample filtrate pH was measured as 4.3 by pH meter, and an additional 20 mL of 0.1N HCl was added to the reaction mixture. The heating controller was turned off and the mixture was allowed to cool to 19° C. and stirred for 18 hours. The reaction was then filtered with a sintered glass funnel and washed with the mother liquor followed by deionized water (3×330 mL). The cake was dried in a vacuum drying oven set to 45° C. and >30 in. vacuum with a slight nitrogen bleed yielded the title compound (51.76 g, 99% yield). $^1$H NMR (500 MHz, DMSO-d$_6$) δ 14.16 (s, 1H), 7.50-7.55 (m, 1H), 7.25-7.30 (m, 3H), 6.44 (s, 1H), 3.28-3.34 (quint, 1H), 2.69-2.73 (d, 1H), 2.44-2.48 (m, 2H), 2.29 (s, 3H) 2.24-2.27 (m, 2H), 2.04-2.08 (m, 1H), 1.51-1.59 (m, 1H), 1.26 (d, 6H). $^{13}$C NMR (500 MHz, CDCl$_3$) δ 163.46, 162.46, 161.51, 156.70, 152.70, 152.35, 133.41, 132.85, 131.94, 131.03, 129.76, 125.39, 121.61, 116.79, 115.22, 42.69, 37.92, 26.89, 24.68, 23.02, 21.48, 12.30. $^{19}$F NMR (500 MHz, CDCl$_3$) δ −73.62 (s), −113.17 (quint). MS (m/z): 526.3 [M+1]$^+$.

Various exemplary embodiments of the disclosure include, but are not limited to the enumerated embodiments listed below, which can be combined in any number and in any combination that is not technically or logically inconsistent.

Embodiment 1. A method for preparing a halopyrazolylthiazole of formula (Ia)

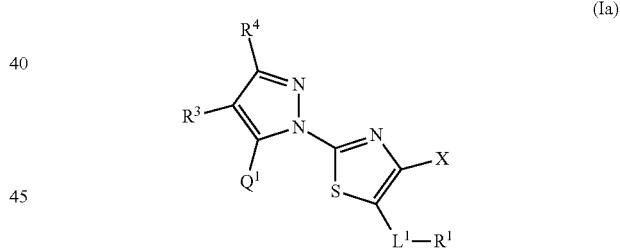

wherein
X is a halogen (e.g., chloro, bromo or iodo);
L$^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;
R$^1$ is selected from the group consisting of C$_1$-C$_8$ alkyl, C$_1$-C$_8$ alkenyl and C$_1$-C$_8$ alkynyl, each unsubstituted or fluorinated;
Q$^1$ is selected from the group consisting of —C(O)OR$^{2C}$, —C(O)NR$^{2B}$R$^{2C}$, —C(O)NR$^{2B}$S(O)$_2$R$^{2C}$, —C(O)NR$^{2B}$S(O)$_2$NR$^{3B}$R$^{2C}$, —S(O)$_2$R$^{2C}$, —N(R$^{2B}$)S(O)$_2$R$^{2C}$, —S(O)$_2$NR$^{2B}$R$^{2C}$, and —C(O)NH—O(C$_1$-C$_3$ alkyl), in which
each R$^{2B}$ is independently selected from H and C$_1$-C$_3$ alkyl, and each $R^{2C}$ is independently selected from $C_1$-$C_3$ alkyl and a protecting group;
$R^3$ is phenyl or heteroaryl each (i) optionally substituted with a single substituent selected from -$L^{3C}$-(phenyl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^D$), -$L^{3C}$-(heterocycloalkyl optionally substituted with 1-5 $R^{3D}$) and (ii) optionally substituted with 1-5 $R^{3E}$,
in which
  each $L^{3C}$ is a bond, methylene, ethylene, —C(O)—, —S—, —S(O)$_{1-2}$—, —O—, or —NR$^{3G}$;
  each $R^3$ is independently selected from oxo optionally-substituted $C_1$-$C_4$ alkyl, $C_1$-$C_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
  each $R^{3E}$ is independently selected from oxo, optionally-substituted $C_1$-$C_4$ alkyl, $C_1$-$C_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
  each $R^{3F}$ is independently selected from H, $C_1$-$C_3$ alkyl and $C_1$-$C_3$ fluoroalkyl and
  each $R^{3G}$ is independently selected from H, $C_1$-$C_3$ alkyl, and $C_1$-$C_3$ fluoroalkyl; and
$R^4$ is selected from the group consisting of hydrogen, optionally substituted $C_1$-$C_8$ alkyl, optionally-substituted $C_1$-$C_8$ alkenyl and optionally substituted $C_1$-$C_8$ alkynyl;
wherein
each $R^6$ is selected from the group consisting of hydrogen, $C_1$-$C_3$ alkyl and —C(O)($C_1$-$C_3$ alkyl);
each optionally substituted alkyl, alkenyl and alkynyl is unsubstituted, fluorinated or substituted with one or two hydroxyl groups;
each cycloalkyl has 3-10 ring carbons and is unsaturated or partially unsaturated;
each heterocycloalkyl has 3-10 ring members and 1-3 heteroatoms independently selected from nitrogen, oxygen and sulfur, and is unsaturated or partially unsaturated; and
each heteroaryl is a 5-6 membered monocyclic heteroaryl ring having 1-3 heteroatoms independently selected from nitrogen, oxygen and sulfur, the method comprising:
reacting a thiazolylhydrazine of formula (Ib)

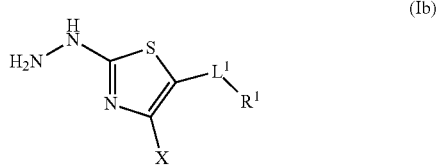

(Ib)

wherein X, $R^1$, and $L^1$ are as described for formula (Ia), with a dione of formula (II)

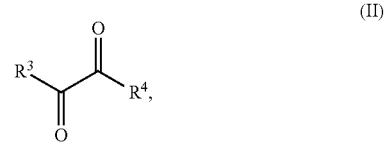

(II)

wherein $R^3$ and $R^4$ are as described for formula (Ia), optionally in a solvent, under conditions sufficient to form a hydrazone; and
contacting the hydrazone with an compound of formula $X^1$—CH$_2$-Q$^1$ wherein Q$^1$ is as described for formula (Ia), and $X^1$ is a halogen or a leaving group, to obtain the halopyrazolylthiazole of formula (Ia).

Embodiment 2. The method of embodiment 1, further comprising preparing the thiazolylhydrazine of formula (Ib) according to the method of any of embodiments 37-46.

Embodiment 3. The method of embodiment 1 or embodiment 2, wherein the amount of the dione is at least 1 molar equivalent based on the amount of the thiazolylhydrazine (e.g., at least 1.1 molar eq., at least 1.25 molar eq., or at least 1.5 molar eq. based on the amount of the thiazole).

Embodiment 4. The method of embodiment 1 or embodiment 2, wherein the thiazolylhydrazine and the dione are reacted at about room temperature.

Embodiment 5. The method of embodiment 5, wherein the thiazolylhydrazine and the dione are reacted for at least 8 hours (e.g., at least 10 hours, at least 12 hours, at least 14 hours, or at least 16 hours); or wherein the thiazolylhydrazine and the dione are reacted for a time in a range of 8 hours to 20 hours (e.g., in a range of 8 hours to 16 hours, 8 hours to 14 hours, 8 hours to 12 hours, 8 hours to 10 hours, 10 hours to 20 hours, 10 hours to 16 hours, 10 hours to 14 hours, 10 hours to 12 hours, 14 hours to 20 hours, 14 hours to 18 hours, 14 hours to 16 hours, 16 hours to 20 hours, 16 hours to 18 hours, or 18 hours to 20 hours).

Embodiment 6. The method of any of embodiments 1-5, wherein the thiazolylhydrazine and the dione are reacted at a temperature of at least 40° C. (e.g., at least 45° C., at least 50° C., at least 60° C., or at least 65° C.); or wherein the thiazolylhydrazine and the dione are reacted at a temperature in a range of 40° C. to 80° C. (e.g., in a range of 40° C. to 70° C., 40° C. to 60° C., 40° C. to 50° C., 50° C. to 80° C., 50° C. to 70° C., 50° C. to 60° C., 60° C. to 80° C., or 60° C. to 70° C.).

Embodiment 7. The method of embodiment 6, wherein the thiazolylhydrazine and the dione are maintained at said temperature for at least 30 minutes (e.g., at least 45 minutes, or at least 1 hour).

Embodiment 8. The method of any of embodiments 1-7, wherein the hydrazone and the alkylhalogenide are reacted in presence of an inorganic iodide and a base.

Embodiment 9. The method of embodiment 8, wherein the inorganic iodide is KI or NaI.

Embodiment 10. The method of embodiment 8 or 9, wherein the amount of inorganic iodide is catalytic based on the amount of the thiazolylhydrazine (e.g., no more than 20 mol %, or no more than 15 mol %, or no more than 10 mol %, or in a range of 5 mol % to 20 mol %, or in a range of 5 mol % to 15 mol %, or in a range of 5 mol % to 10 mol %, or in a range of 8 mol % to 20 mol %, or in a range of 8 mol % to 15 mol %, or in a range of 8 mol % to 12 mol %, or in a range of 8 mol % to 10 mol %, or in a range of 10 mol % to 20 mol %, or in a range of 10 mol % to 15 mol %, based on the amount of the thiazolylhydrazine).

Embodiment 11. The method of embodiment 8 or embodiment 9, wherein the amount of inorganic iodide is stoichiometric based on the amount of the thiazole (e.g., at least 1 molar equivalent based on the amount of the thiazole).

Embodiment 12. The method of any of embodiments 8-11, wherein the base is a carbonate (e.g., potassium carbonate).

Embodiment 13. The method of any of embodiments 1-12, wherein the hydrazone and the alkylhalogenide are reacted at a temperature of at least 80° C. (e.g., at least 85° C., at least 90° C., at least 95° C., at least 100° C., or at least 110° C.); or hydrazone and the alkylhalogenide are reacted at a temperature in a range of 80° C. to 120° C. (e.g., in a range of 80° C. to 110° C., 80° C. to 100° C., 80° C. to 90° C., 90° C. to 120° C., 90° C. to 110° C., 90° C. to 100° C., 100° C. to 120° C., or 100° C. to 110° C.).

Embodiment 14. The method of any of embodiments 1-13, wherein the hydrazone and the alkylhalogenide are contacted for at least 8 hours (e.g., at least 10 hours, at least 12 hours, at least 14 hours, or at least 16 hours); or wherein the hydrazone and the alkylhalogenide are contacted for a time in a range of 8 hours to 24 hours (e.g., in a range of 8 hours to 20 hours, 8 hours to 16 hours, 8 hours to 14 hours, 8 hours to 12 hours, 8 hours to 10 hours, 10 hours to 24 hours, 10 hours to 20 hours, 10 hours to 16 hours, 10 hours to 14 hours, 10 hours to 12 hours, 14 hours to 24 hours, 14 hours to 20 hours, 14 hours to 18 hours, 14 hours to 16 hours, 16 hours to 24 hours, 16 hours to 20 hours, 16 hours to 18 hours, 18 hours to 24 hours, or 18 hours to 20 hours).

Embodiment 15. The method of any of embodiments 1-14 wherein the reaction of the thiazolylhydrazine with the dione to form the hydrazone and the reaction of the hydrazone with the alkylhalogenide of formula $X^1$—$CH_2$-$Q^1$ to form the halopyrazolylthiazole are performed without isolation or purification of any intermediate.

Embodiment 16. The method of any of embodiments 1-15, further comprising crystalizing the halopyrazolylthiazole of formula (Ia) from an alcohol to obtain the compound having purity of at least 98%.

Embodiment 17. A halopyrazolylthiazole of formula (Ia)

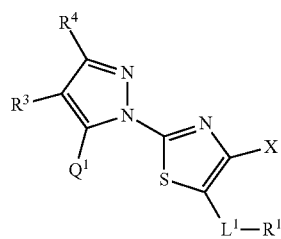

(Ia)

wherein
X is a halogen;
$L^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;
$R^1$ is selected from the group consisting of $C_1$-$C_8$ alkyl, $C_1$-$C_8$ alkenyl and $C_1$-$C_8$ alkynyl, each unsubstituted or fluorinated;

$Q^1$ is selected from the group consisting of —C(O)OR$^{2C}$, —C(O)NR$^{2B}$R$^{2C}$, —C(O)NR$^{2B}$S(O)$_2$R$^{2C}$, —C(O)NR$^{2B}$S(O)$_2$NR$^{2B}$R$^{2C}$, —S(O)$_2$R$^{2C}$, —N(R$^{2B}$)S(O)$_2$R$^{2C}$, —S(O)$_2$NR$^{2B}$R$^{2C}$, and —C(O)NH—O(C$_1$-C$_3$ alkyl), in which
each R$^{2B}$ is independently selected from H and $C_1$-$C_3$ alkyl, and
each R$^{2C}$ is independently selected from $C_1$-$C_3$ alkyl and a protecting group;
$R^3$ is phenyl or heteroaryl each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5
R$^D$), -L$^{3C}$-(heterocycloalkyl optionally substituted with 1-5 R$^{3D}$) and (ii) optionally substituted with 1-5 R$^{3E}$,
in which
each L$^{3C}$ is a bond, methylene, ethylene, —C(O)—, —S—, —S(O)$_{1-2}$—, —O—, or —NR$^{3G}$—;
each R$^{3D}$ is independently selected from oxo optionally-substituted $C_1$-$C_4$ alkyl, $C_1$-$C_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
each R$^{3E}$ is independently selected from oxo, optionally-substituted $C_1$-$C_4$ alkyl, $C_1$-$C_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
each R$^{3F}$ is independently selected from H, $C_1$-$C_3$ alkyl and $C_1$-$C_3$ fluoroalkyl and
each R$^{3G}$ is independently selected from H, $C_1$-$C_3$ alkyl, and $C_1$-$C_3$ fluoroalkyl; and
$R^4$ is selected from the group consisting of hydrogen, optionally substituted $C_1$-$C_8$ alkyl, optionally-substituted $C_1$-$C_8$ alkenyl and optionally substituted $C_1$-$C_8$ alkynyl;
wherein
each R$^6$ is selected from the group consisting of hydrogen, $C_1$-$C_3$ alkyl and —C(O)(C$_1$-$C_3$ alkyl);
each optionally substituted alkyl, alkenyl and alkynyl is unsubstituted, fluorinated or substituted with one or two hydroxyl groups;
each cycloalkyl has 3-10 ring carbons and is unsaturated or partially unsaturated;
each heterocycloalkyl has 3-10 ring members and 1-3 heteroatoms independently selected from nitrogen, oxygen and sulfur, and is unsaturated or partially unsaturated; and
each heteroaryl is a 5-6 membered monocyclic heteroaryl ring having 1-3 heteroatoms independently selected from nitrogen, oxygen and sulfur, Embodiment 18. The method or compound of any of embodiments 1-17, wherein X is Cl.

Embodiment 19. The method or compound of any of embodiments 1-17, wherein X is Br.

Embodiment 20. The method or compound of any of embodiments 1-17, wherein X is 1.

Embodiment 21. The method or compound of any of embodiments 1-17, wherein the halopyrazolylthiazole of formula (Ia) is $C_1$-$C_3$ alkyl 1-(4-halo-5-(isopropylthio)thiazol-2-yl)-4-(3-fluorophenyl)-3-methyl-1H-pyrazole-5-carboxylate (such as ethyl 1-(4-bromo-5-(isopropylthio)thiazol-2-yl)-4-(3-fluorophenyl)-3-methyl-1H-pyrazole-5-carboxylate).

Embodiment 22. A method for preparing a compound of formula (I)

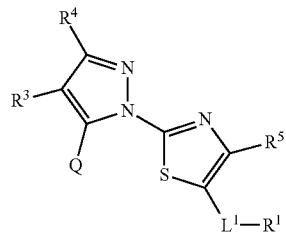

(I)

optionally in the form of a pharmaceutically acceptable salt or N-oxide, and/or a solvate or hydrate, wherein $L^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$;

$R^1$ is selected from the group consisting of $C_1$-$C_8$ alkyl, $C_1$-$C_8$ alkenyl and $C_1$-$C_8$ alkynyl, each unsubstituted or fluorinated;

Q is selected from the group consisting of —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —S(O)$_2$R$^{2A}$, —N(R$^{2B}$)S(O)$_2$R$^{2A}$, —S(O)$_2$NR$^{2B}$R$^{2A}$, and —C(O)NH—O($C_1$-$C_3$ alkyl), in which each $R^{2A}$ is independently selected from H, $C_1$-$C_3$ alkyl, and a protecting group, and each $R^{2B}$ is independently selected from H and $C_1$-$C_3$ alkyl;

$R^3$ is phenyl or heteroaryl each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^{3E}$, in which each L$^{3C}$ is a bond, methylene, ethylene, —C(O)—, —S—, —S(O)$_{1-2}$—, —O—, or —NR$^{3G}$—;

each R$^{3D}$ is independently selected from oxo optionally-substituted $C_1$-$C_4$ alkyl, $C_1$-$C_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^3$S(O)$_{1-2}$R$^{3F}$;

each R$^{3E}$ is independently selected from oxo, optionally-substituted $C_1$-$C_4$ alkyl, $C_1$-$C_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3F}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;

each R$^{3F}$ is independently selected from H, $C_1$-$C_3$ alkyl and $C_1$-$C_3$ fluoroalkyl and each R$^{3G}$ is independently selected from H, $C_1$-$C_3$ alkyl, and $C_1$-$C_3$ fluoroalkyl;

$R^4$ is selected from the group consisting of hydrogen, optionally substituted $C_1$-$C_8$ alkyl, optionally-substituted $C_1$-$C_8$ alkenyl and optionally substituted $C_1$-$C_8$ alkynyl; and $R^5$ is phenyl, heteroaryl, cycloalkyl or heterocycloalkyl, each optionally substituted with 1-5 R$^{5E}$, in which each R$^{5E}$ is independently selected from oxo, optionally-substituted $C_1$-$C_4$ alkyl, $C_1$-$C_4$ fluoroalkyl, halogen, —CN, —SF$_5$, —N$_3$, —C(O)R$^1$, —SR$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{5G}$R$^{5F}$, —NR$^{5G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, —C(S)SR$^{5F}$, —SC(S)R$^{5F}$, —S(O)$_{1-2}$OR$^{5F}$, —OS(O)$_{1-2}$R$^{5F}$, —S(O)$_{1-2}$NR$^{5G}$R$^{5F}$, and —NR$^{5G}$S(O)$_{1-2}$R$^{5F}$;

each R$^{5F}$ is independently selected from H, $C_1$-$C_3$ alkyl and $C_1$-$C_3$ fluoroalkyl and each R$^{5G}$ is independently selected from H and $C_1$-$C_3$ alkyl;

wherein each R$^6$ is selected from the group consisting of hydrogen, $C_1$-$C_3$ alkyl and —C(O)($C_1$-$C_3$ alkyl);

each optionally substituted alkyl, alkenyl and alkynyl is unsubstituted, fluorinated or substituted with one or two hydroxyl groups;

each cycloalkyl has 3-10 ring carbons and is unsaturated or partially unsaturated;

each heterocycloalkyl has 3-10 ring members and 1-3 heteroatoms independently selected from nitrogen, oxygen and sulfur, and is unsaturated or partially unsaturated;

each heteroaryl is a 5-6 membered monocyclic heteroaryl ring having 1-3 heteroatoms independently selected from nitrogen, oxygen and sulfur, the method comprising:
coupling a halopyrazolylthiazole of formula (Ia)

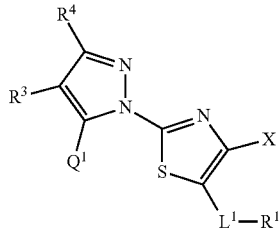

wherein X is a halogen (e.g., Cl, Br or I);
Q$^1$ is selected from the group consisting of —C(O)OR$^{2C}$, —C(O)NR$^{2B}$R$^{2C}$, —C(O)NR$^{2B}$S(O)$_2$R$^{2C}$, —C(O)NR$^{2B}$S(O)$_2$NR$^{2B}$R$^{2C}$, —S(O)$_2$R$^{2C}$, —N(R$^{2'}$)S(O)$_2$R$^{2C}$, —S(O)$_2$NR$^{2B}$R$^{2C}$, and —C(O)NH—O(C$_1$-C$_3$ alkyl), in which
each R$^{2B}$ is independently selected from H and C$_1$-C$_3$ alkyl, and
each R$^{2C}$ is independently selected from C$_1$-C$_3$ alkyl and a protecting group;
and L$^1$, R$^1$, R$^3$, and R$^4$ are as described for formula (I).
optionally in a solvent, with an organoboron comprising R$^5$ moiety to obtain the compound of formula (I).

Embodiment 23. The method of embodiment 22, further comprising preparing the halopyrazolylthiazole of formula (Ia) according to the method any of embodiments 1-21.

Embodiment 24. The method of embodiment 22 or 23, wherein the organoboron is an boronic acid or boronic ester having R$^5$ substituted on the boron atom.

Embodiment 25. The method of embodiment 24, wherein the organoboron has the formula:

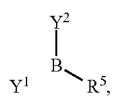

wherein
R$^5$ is as described for formula (I), and
Y$^1$ and Y$^2$ are independently hydroxy or C$_1$-C$_4$ alkoxy, or Y$^1$ and Y$^2$ together with B atom form a 5- or 6-membered ring having one or two oxygens in the ring bound to the boron.

Embodiment 26. The method of any of embodiments 22-25, wherein coupling is carried out under Suzuki conditions.

Embodiment 27. The method of any of embodiments 22-25, wherein the halpyrazolylthiazole of formula (Ia) and the organoboron are coupled in presence of a palladium catalyst and a base.

Embodiment 28. The method of embodiment 27, wherein the palladium catalyst is [1,1'-bis(diphenylphosphino)ferrocene]dichloropalladium(II).

Embodiment 29. The method of embodiment 27 or 28, wherein the base is a carbonate (e.g., potassium carbonate).

Embodiment 30. The method of any of embodiments 22-29, wherein the coupling is at a temperature of at least 80° C. (e.g., at least 85° C., at least 90° C., at least 95° C., at least 100° C., or at least 110° C.); or coupling is at a temperature in a range of 80° C. to 120° C. (e.g., in a range of 80° C. to 110° C., 80° C. to 100° C., 80° C. to 90° C., 90° C. to 120° C., 90° C. to 110° C., 90° C. to 100° C., 100° C. to 120° C., or 100° C. to 110° C.).

Embodiment 31. The method of any of embodiments 22-30, wherein the coupling is for at least 8 hours (e.g., at least 10 hours, at least 12 hours, at least 14 hours, or 1 at least 6 hours); or wherein the coupling is for a time in a range of 8 hours to 24 hours (e.g., in a range of 8 hours to 20 hours, 8 hours to 16 hours, 8 hours to 14 hours, 8 hours to 12 hours, 8 hours to 10 hours, 10 hours to 24 hours, 10 hours to 20 hours, 10 hours to 16 hours, 10 hours to 14 hours, 10 hours to 12 hours, 14 hours to 24 hours, 14 hours to 20 hours, 14 hours to 18 hours, 14 hours to 16 hours, 16 hours to 24 hours, 16 hours to 20 hours, 16 hours to 18 hours, 18 hours to 24 hours, or 18 hours to 20 hours).

Embodiment 32. The method of any of embodiments 22-31, wherein the compound of formula (I) is

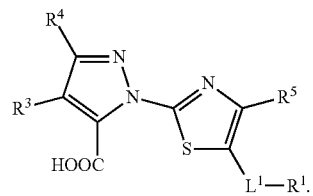

Embodiment 33. The method of embodiment 32 further comprising hydrolyzing the compound of formula (I) (e.g., wherein Q$^1$ is —C(O)O(C$_1$-C$_3$ alkyl)) to obtain the carboxylic acid compound of formula (I).

Embodiment 34. The method of embodiment 32 further comprising hydrolyzing the compound of formula (I) (e.g., wherein Q$^1$ is —C(O)O(C$_1$-C$_3$ alkyl)) to obtain a carboxylate salt of the compound of formula (I).

Embodiment 35. The method of embodiment 34 further comprising crystallizing the salt of the compound of formula (I); and protonating the salt of the compound of formula (I) with an acid to obtain the compound of formula (I) having purity of at least 98%.

Embodiment 36. The method of any of embodiments 33-35, wherein the compound of formula (I) is 4-(3-fluorophenyl)-1-(5-(isopropylthio)-4-(4-(trifluoromethyl)cyclohex-1-en-1-yl)thiazol-2-yl)-3-methyl-1H-pyrazole-5-carboxylic acid, optionally in the form of a pharmaceutically acceptable salt, and/or a solvate or hydrate.

Embodiment 37. A method for preparing a thiazolylhydrazine of formula (Ib)

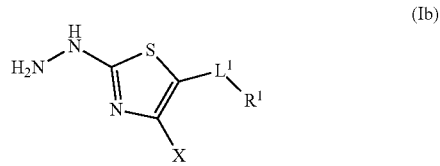

wherein
X is a halogen (e.g., chloro, bromo or iodo);
L$^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;
R$^1$ is selected from the group consisting of C$_1$-C$_8$ alkyl, C$_1$-C$_8$ alkenyl and C$_1$-C$_8$ alkynyl, each unsubstituted or fluorinated;
wherein
  each R$^6$ is selected from the group consisting of hydrogen, C$_1$-C$_3$ alkyl and —C(O)(C$_1$-C$_3$ alkyl);
the method comprising:
  reacting a dihalothiazole of formula

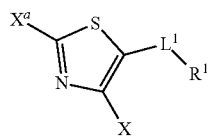

wherein X, R$^1$, and L$^1$ are as described for formula (Ib), and X$^a$ is halogen (for example, chloro, bromo or iodo, e.g., chloro), optionally in a solvent, with an aqueous solution of hydrazine to obtain a crude product; and
crystallizing the crude product to obtain the thiazolylhydrazine of formula (Ib).

Embodiment 38. The method of embodiment 37, wherein X$^a$ is chloro.
Embodiment 39. The method of embodiment 37, wherein X$^a$ is bromo.
Embodiment 40. The method of embodiment 37, wherein X$^a$ is iodo.
Embodiment 41. The method of any of embodiments 37-40, wherein the amount of hydrazine is at least 5 molar equivalent based on the amount of the dihalothiazole (e.g., at least 5.25 molar equivalent, e.g., at least 5.5 molar equivalent, at least 5.5 molar equivalent, or at least 6 molar equivalent based on the amount of the dihalothiazole).
Embodiment 42. The method of any of embodiments 37-41, wherein the solvent is tetrahydrofuran, ethyl acetate, acetone, dimethylformamide, acetonitrile, or dimethyl sulfoxide; e.g., tetrahydrofuran.
Embodiment 43. The method of any of embodiments 37-42, wherein the reaction of the dihalothiazole with the hydrazine is at about room temperature (e.g., in a range of 20° C. to 25° C., or 20° C. to 23° C.).
Embodiment 44. The method of any of embodiments 37-43, wherein the reacting is for at least 10 hours (e.g., at least 20 hours, at least 24 hours, at least 48 hours, or at least 72 hours), for example, for a time in a range of 10 hours to 100 hours.
Embodiment 45. The method of any of embodiments 37-44, wherein the crystallization is from hydrocarbon solvent (e.g., hexanes, heptanes, or a combination thereof).
Embodiment 46. The method of any of embodiments 37-44, wherein the crystallization is from hydrocarbon solvent (e.g., hexanes, heptanes, or a combination thereof) in an amount of about 100% v/v to 300% v/v, based on total volume of the crude product.
Embodiment 47. The method or compound of any of embodiments 1-46, wherein R$^1$ is optionally substituted C$_1$-C$_8$ alkyl.
Embodiment 48. The method or compound of any of embodiments 1-46, wherein R$^1$ is unsubstituted C$_1$-C$_8$ alkyl or fluorinated C$_1$-C$_8$ alkyl.
Embodiment 49. The method or compound of any of embodiments 1-46, wherein R$^1$ is unsubstituted C$_1$-C$_8$ alkyl; or wherein R$^1$ is optionally substituted C$_1$-C$_5$ alkyl.

Embodiment 50. The method or compound of any of embodiments 1-46, wherein R$^1$ is unsubstituted C$_1$-C$_5$ alkyl or fluorinated C$_1$-C$_5$ alkyl.
Embodiment 51. The method or compound of any of embodiments 1-46, wherein R$^1$ is unsubstituted C$_1$-C$_5$ alkyl.
Embodiment 52. The method or compound of any of embodiments 1-46, wherein R$^1$ is optionally substituted C$_1$-C$_5$ alkyl.
Embodiment 53. The method or compound of any of embodiments 1-46, wherein R$^1$ is unsubstituted C$_1$-C$_5$ alkyl or fluorinated C$_1$-C$_5$ alkyl.
Embodiment 54. The method or compound of any of embodiments 1-46, wherein R$^1$ is unsubstituted C$_1$-C$_5$ alkyl.
Embodiment 55. The method or compound of any of embodiments 1-46, wherein R$^1$ is hydroxymethyl, methoxymethyl, hydroxyethyl or methoxyethyl.
Embodiment 56. The method or compound of any of embodiments 1-46, wherein R$^1$ is methyl, ethyl, propyl, isopropyl, butyl, or tert-butyl.
Embodiment 57. The method or compound of any of embodiments 1-46, wherein R$^1$ is propyl, isopropyl, butyl, or tert-butyl.
Embodiment 58. The method or compound of any of embodiments 1-46, wherein R$^1$ is isopropyl.
Embodiment 59. The method or compound of any of embodiments 1-58, wherein L$^1$ is a bond, —O—, —S—, —S(O)—, or —S(O)$_2$.
Embodiment 60. The method or compound of any of embodiments 1-58, wherein L$^1$ is —O—, —S—, —S(O)—, or —S(O)$_2$.
Embodiment 61. The method or compound of any of embodiments 1-58, wherein L$^1$ is —S—, —S(O)—, or —S(O)$_2$.
Embodiment 62. The method or compound of any of embodiments 1-58, wherein L$^1$ is —S—.
Embodiment 63. The method or compound of any of embodiments 1-58, wherein or wherein L$^1$ is a bond.
Embodiment 64. The method or compound of any of embodiments 1-58, wherein L$^1$ is —O.
Embodiment 65. The method or compound of any of embodiments 1-58, wherein L$^1$ is —NR$^6$—.
Embodiment 66. The method or compound of any of embodiments 1-35 or 47-65, wherein R$^3$ is aryl (e.g., a phenyl) optionally substituted with 1-5 R$^{3E}$.
Embodiment 67. The method or compound of any of embodiments 1-35 or 47-65, wherein R$^3$ is aryl (e.g., a phenyl) optionally substituted with 1-2 R$^{3E}$.
Embodiment 68. The method or compound of any of embodiments 1-35 or 47-65, wherein R$^3$ is aryl (e.g., a phenyl) optionally substituted with R$^{3E}$.
Embodiment 69. The method or compound of any of embodiments 1-35 or 47-65, wherein R$^3$ is aryl (e.g., a phenyl) substituted with 1-2 R$^{3E}$.
Embodiment 70. The method or compound of any of embodiments 1-35 or 47-65, wherein R$^3$ is aryl (e.g., a phenyl) substituted with R$^{3E}$.
Embodiment 71. The method or compound of any of embodiments 1-35 or 47-65, wherein R$^3$ is heteroaryl (e.g., an isothiazole, a pyridone, a thiadiazole, a pyrazine, an imidazole, a pyridine, a pyrazole, an isoxazole, a thiophene, a furan or a pyrimidine) optionally substituted with 1-5 R$^{3E}$.
Embodiment 72. The method or compound of any of embodiments 1-35 or 47-65, wherein R$^3$ is selected from the group consisting of phenyl and monocyclic heteroaryl (e.g., pyridyl, pyrazolyl), optionally substituted with 1-5 R$^{3E}$; or wherein R$^3$ is phenyl substituted with a halogen.

Embodiment 73. The method or compound of any of embodiments 1-35 or 47-65, wherein $R^3$ is 3-fluorophenyl.

Embodiment 74. The method or compound of any of embodiments 1-35 or 47-65, wherein $R^3$ is phenyl or heteroaryl, each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3D}$), -$L^{3C}$-(heterocycloalkyl optionally substituted with 1-5 $R^{3D}$) and (ii) optionally substituted with 1-5 $R^{3E}$.

Embodiment 75. The method or compound of any of embodiments 1-35 or 47-65, wherein $R^3$ is phenyl (i) substituted with a single substituent selected from -$L^{3C}$-(phenyl optionally substituted with 1-5 $R^0$), -$L^{3C}$-(heteroaryl optionally substituted with 1-5 $R^{3D}$), -$L^{3C}$-(cycloalkyl optionally substituted with 1-5 $R^{30}$), -$L^{3C}$-(heterocycloalkyl optionally substituted with 1-5 $R^3$) and (ii) optionally substituted with 1-5 $R^{3E}$.

Embodiment 76. The method or compound of any of embodiments 1-35 or 47-65, wherein $R^3$ is heteroaryl (e.g., an isothiazole, a pyridone, a thiadiazole, a pyrazine, a pyridine, a pyrazole, an isoxazole, a a thiophene, a furan or a pyrimidine) (i) substituted with a single substituent selected from -$L^{3C}$-(phenyl optionally substituted with 1-5 $R^{3D}$), -$L^{3C}$-(heteroaryl optionally substituted with 1-5 $R^{3D}$), -$L^{3C}$-(monocyclic cycloalkyl optionally substituted with 1-5 $R^{3D}$), -$L^{3C}$-(monocyclic heterocycloalkyl optionally substituted with 1-5 $R^{3D}$) and (ii) optionally substituted with 1-5 $R^{3E}$.

Embodiment 77. The method or compound of any of embodiments 1-35 or 47-76, wherein each $R^{3E}$ is independently selected from $C_1$-$C_4$ alkyl, $C_1$-$C_4$ fluoroalkyl, halogen, —$OR^{3F}$, and —$NR^{3G}R^{3F}$; or wherein $R^{3E}$ is independently selected from halogen, —$OR^{3F}$, and —$NR^{3G}R^{3F}$.

Embodiment 78. The method or compound of any of embodiments 1-35 or 47-76, wherein each $R^{3E}$ is independently selected from $C_1$-$C_4$ alkyl, $C_1$-$C_4$ fluoroalkyl, and halogen.

Embodiment 79. The method or compound of any of embodiments 1-35 or 47-76, wherein each $R^{3E}$ is independently selected from $C_1$-$C_4$ alkyl, halogen, —$OR^{3F}$, and —$NR^{3G}R^{3F}$.

Embodiment 80. The method or compound of any of embodiments 1-35 or 47-76, wherein each $R^{3E}$ is independently selected from $C_1$-$C_4$ fluoroalkyl and halogen.

Embodiment 81. The method or compound of any of embodiments 1-35 or 47-76, wherein each $R^{3E}$ is independently halogen.

Embodiment 82. The method or compound of any of embodiments 1-35 or 47-81, wherein $R^4$ is optionally substituted $C_1$-$C_8$ alkyl, optionally-substituted $C_1$-$C_8$ alkenyl or optionally substituted $C_1$-$C_8$ alkynyl.

Embodiment 83. The method or compound of any of embodiments 1-35 or 47-81, wherein $R^4$ is optionally substituted $C_1$-$C_8$ alkyl.

Embodiment 84. The method or compound of any of embodiments 1-35 or 47-81, wherein $R^4$ is hydrogen or unsubstituted $C_1$-$C_8$ alkyl.

Embodiment 85. The method or compound of any of embodiments 1-35 or 47-81, wherein $R^4$ is unsubstituted $C_1$-$C_3$ alkyl.

Embodiment 86. The method or compound of any of embodiments 1-35 or 47-81, wherein $R^4$ is unsubstituted methyl.

Embodiment 87. The method or compound of any of embodiments 22-35 or 47-86, wherein $R^5$ is unsaturated cycloalkyl optionally substituted with 1-5 $R^{5E}$.

Embodiment 88. The method or compound of any of embodiments 22-35 or 47-86, wherein $R^5$ is unsaturated cycloalkyl is substituted with 1-5 $R^{5E}$.

Embodiment 89. The method of any or compound of embodiments 22-35 or 47-86, wherein $R^5$ is cyclohexen-1-yl substituted with $R^{5E}$.

Embodiment 90. The method or compound of any of embodiments 22-35 or 47-86, wherein $R^5$ is 4-(trifluoromethyl)cyclohex-1-en-1-yl.

Embodiment 91. The method or compound of any of embodiments 22-35 or 47-86, wherein $R^5$ is phenyl optionally substituted with 1-5 $R^{5E}$.

Embodiment 92. The method or compound of any of embodiments 22-35 or 47-86, wherein $R^5$ is heteroaryl (e.g., an isoxazolyl, a pyridyl, an imidazopyridyl, a pyrazolyl), each optionally substituted with 1-5 $R^{5E}$.

Embodiment 93. The method or compound of any of embodiments 22-35 or 47-86, wherein $R^5$ is heterocycloalkyl optionally substituted with 1-5 $R^{5E}$.

Embodiment 94. The method or compound of any of embodiments 22-35 or 47-86, wherein $R^5$ is cycloalkyl optionally substituted with 1-5 $R^{5E}$.

Embodiment 95. The method or compound of any of embodiments 22-35 or 47-86, wherein $R^5$ is cycloalkyl substituted with 1-5 $R^{5E}$.

Embodiment 96. The method or compound of any of embodiments 22-35 or 47-86, wherein $Q^1$ is —$C(O)OR^{2C}$.

Embodiment 97. The method or compound of any of embodiments 1-36 or 47-96, wherein $Q^1$ is —$C(O)NR^{2B}R^{2C}$.

Embodiment 98. The method or compound of any of embodiments 1-36 or 47-96, $Q^1$ is —$C(O)O(C_1$-$C_3$ alkyl), e.g., —$C(O)O(ethyl)$.

Embodiment 99. The method or compound of any of embodiments 1-36 or 47-96, $Q^1$ is —$C(O)OR^{2C}$ and $R^{2C}$ is a protecting group.

Embodiment 100. The method or compound of any not-inconsistent embodiment above, wherein the compound of formula (Ia) is:

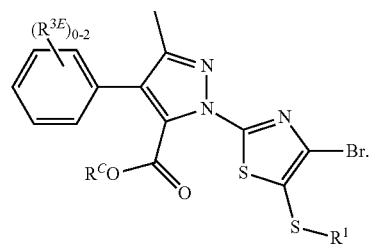

Embodiment 101. The method or compound of any not-inconsistent embodiment above, wherein the compound of formula (Ia) is:

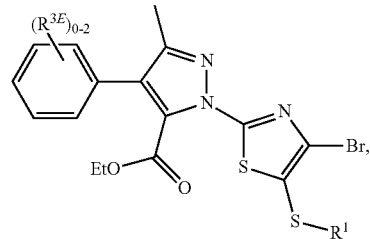

wherein $R^1$ is $C_1$-$C_8$ alkyl, and $R^{3E}$ is independently selected from $C_1$-$C_4$ alkyl, $C_1$-$C_4$ fluoroalkyl, halogen, —$OR^{3F}$, and —$NR^{3G}R^{3F}$.

Embodiment 102. The method or compound of any not-inconsistent embodiment above, wherein Q is —$C(O)OR^{2A}$ or —$C(O)NR^{2B}R^{2A}$; or wherein Q is —$C(O)OR^{2A}$; or wherein Q is —C(O)OH or —$C(O)O(C_1$-$C_3$ alkyl); or wherein Q is —C(O)OH.

Embodiment 103. The compound, which is ethyl 1-(4-bromo-5-(isopropylthio)thiazol-2-yl)-4-(3-fluorophenyl)-3-methyl-1H-pyrazole-5-carboxylate.

Numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method for preparing a halopyrazolylthiazole of formula (Ia)

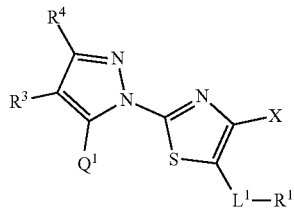

(Ia)

wherein
X is a halogen;
$L^1$ is selected from the group consisting of a bond, —C(O)—, —S—, —$S(O)_{1-2}$—, —O—, —$NR^6$—, —C(O)$NR^6$—, —$NR^6$C(O)—, —C(S)$NR^6$—, —$NR^6$C(S)—, —C(O)O—, —OC(O)—, —C(O)S—, —SC(O)—, —C(S)O—, —OC(S)—, —C(S)S—, —SC(S)—, —$S(O)_{1-2}$O—, —$OS(O)_{1-2}$—, —$S(O)_{1-2}NR^6$— and —$NR^6S(O)_{1-2}$—;
$R^1$ is selected from the group consisting of $C_1$-$C_8$ alkyl, $C_1$-$C_8$ alkenyl and $C_1$-$C_8$ alkynyl, each unsubstituted or fluorinated;
$Q^1$ is selected from the group consisting of —C(O)$OR^{2C}$, —C(O)$NR^{2B}R^{2C}$, —C(O)$NR^{2B}S(O)_2R^{2C}$, —C(O)$NR^{2B}S(O)_2NR^{2B}R^{2C}$, —$S(O)_2R^{2C}$, —$N(R^{2B})S(O)_2R^{2C}$, —$S(O)_2NR^{2B}R^{2C}$, and —C(O)NH—$O(C_1$-$C_3$ alkyl), in which
each $R^{2B}$ is independently selected from H and $C_1$-$C_3$ alkyl, and
each $R^{2C}$ is independently selected from $C_1$-$C_3$ alkyl and a protecting group;
$R^3$ is phenyl or heteroaryl each (i) optionally substituted with a single substituent selected from -$L^{3C}$-(phenyl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3D}$), -$L^{3C}$-(heterocycloalkyl optionally substituted with 1-5 $R^{3D}$) and (ii) optionally substituted with 1-5 $R^{3E}$, in which
each $L^{3C}$ is a bond, methylene, ethylene, —C(O)—, —S—, —$S(O)_{1-2}$—, —O—, or —$NR^{3G}$—;
each $R^{3D}$ is independently selected from oxo optionally-substituted $C_1$-$C_4$ alkyl, $C_1$-$C_4$ fluoroalkyl, halogen, —CN, —$SF_5$, —$N_3$, —$C(O)R^{3F}$, —$SR^{3F}$, —$S(O)_{1-2}R^{3F}$, —$OR^{3F}$, —$NR^{3G}R^{3F}$, —$C(O)R^{3F}$, —$C(O)NR^{3G}R^{3F}$, —$NR^{3G}C(O)R^{3F}$, —$C(S)NR^{3G}R^{3F}$, —$NR^{3G}C(S)R^{3F}$, —$C(O)OR^{3F}$, —$OC(O)R^{3F}$, —$C(O)SR^{3F}$, —$SC(O)R^{3F}$, —$C(S)OR^{3F}$, —$OC(S)R^{3F}$, —$C(S)SR^{3F}$, —$SC(S)R^{3F}$, —$S(O)_{1-2}OR^{3F}$, —$OS(O)_{1-2}R^{3F}$, —$S(O)_{1-2}NR^{3G}R^{3F}$, and —$NR^{3G}S(O)_{1-2}R^{3F}$;
each $R^{3E}$ is independently selected from oxo, optionally-substituted $C_1$-$C_4$ alkyl, $C_1$-$C_4$ fluoroalkyl, halogen, —CN, —$SF_5$, —$N_3$, —$C(O)R^{3F}$, —$SR^{3F}$, —$S(O)_{1-2}R^{3F}$, —$OR^{3F}$, —$NR^{3G}R^{3F}$, —$C(O)R^{3F}$, —$C(O)NR^{3G}R^{3F}$, —$NR^{3G}C(O)R^{3F}$, —$C(S)NR^{3G}R^{3F}$, —$NR^{3G}C(S)R^{3F}$, —$C(O)OR^{3F}$, —$OC(O)R^{3F}$, —$C(O)SR^{3F}$, —$SC(O)R^{3F}$, —$C(S)OR^{3F}$, —$OC(S)R^{3F}$, —$C(S)SR^{3F}$, —$SC(S)R^{3F}$, —$S(O)_{1-2}OR^{3F}$, —$OS(O)_{1-2}R^{3F}$, —$S(O)_{1-2}NR^{3G}R^{3F}$, and —$NR^{3G}S(O)_{1-2}R^{3F}$;
each $R^{3F}$ is independently selected from H, $C_1$-$C_3$ alkyl and $C_1$-$C_3$ fluoroalkyl and
each $R^{3G}$ is independently selected from H, $C_1$-$C_3$ alkyl, and $C_1$-$C_3$ fluoroalkyl; and
$R^4$ is selected from the group consisting of hydrogen, optionally substituted $C_1$-$C_8$ alkyl, optionally-substituted $C_1$-$C_8$ alkenyl and optionally substituted $C_1$-$C_8$ alkynyl;

wherein
each $R^6$ is selected from the group consisting of hydrogen, $C_1$-$C_3$ alkyl and —$C(O)(C_1$-$C_3$ alkyl);
each optionally substituted alkyl, alkenyl and alkynyl is unsubstituted, fluorinated or substituted with one or two hydroxyl groups;
each cycloalkyl has 3-10 ring carbons and is saturated or partially unsaturated;
each heterocylcloalkyl has 3-10 ring members and 1-3 heteroatoms independently selected from nitrogen, oxygen and sulfur, and is saturated or partially unsaturated; and
each heteroaryl is a 5-6 membered monocyclic heteroaryl ring having 1-3 heteroatoms independently selected from nitrogen, oxygen and sulfur, the method comprising:
reacting a thiazolylhydrazine of formula (Ib)

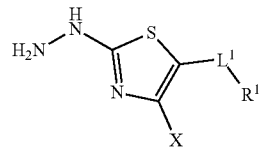

(Ib)

wherein X, R¹, and L¹ are as described for formula (Ia),
with a dione of formula (II)

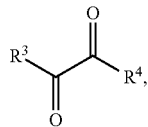

(II)

wherein R³ and R⁴ are as described for formula (Ia), optionally in a solvent, under conditions sufficient to form a hydrazone; and
contacting the hydrazone with an compound of formula X¹—CH₂-Q¹ wherein Q¹ is as described for formula (Ia), and X¹ is a halogen or a leaving group, to obtain the halopyrazolylthiazole of formula (Ia).

2. The method of claim 1, wherein the hydrazone and the alkylhalogenide are reacted in presence of an inorganic iodide and a base.

3. The method of claim 2, wherein the inorganic iodide is KI or NaI.

4. The method of claim 2, wherein the amount of inorganic iodide at least 1 molar equivalent based on the amount of the thiazole.

5. The method of claim 2, wherein the base is a carbonate.

6. A halopyrazolylthiazole of formula (Ia)

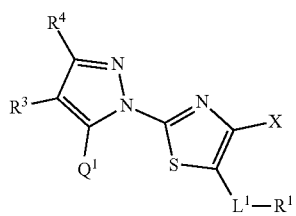

(Ia)

wherein
X is a halogen;
L¹ is selected from the group consisting of a bond, —C(O)—, —S—, —S(O)$_{1-2}$—, —O—, —NR⁶—, —C(O)NR⁶—, —NR⁶C(O)—, —C(S)NR⁶—, —NR⁶C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR⁶— and —NR⁶S(O)$_{1-2}$—;
R¹ is selected from the group consisting of C₁-C₈ alkyl, C₁-C₈ alkenyl and C₁-C₈ alkynyl, each unsubstituted or fluorinated;
Q¹ is selected from the group consisting of —C(O)OR$^{2C}$, —C(O)NR$^{2B}$R$^{2C}$, —C(O)NR$^{2B}$S(O)₂R$^{2C}$, —C(O)NR$^{2B}$S(O)₂NR$^{2B}$R$^{2C}$, —S(O)₂R$^{2C}$, —N(R$^{2B}$)S(O)₂R$^{2C}$, —S(O)₂NR$^{2B}$R$^{2C}$, and —C(O)NH—O(C₁-C₃ alkyl), in which
each R$^{2B}$ is independently selected from H and C₁-C₃ alkyl, and
each R$^{2C}$ is independently selected from C₁-C₃ alkyl and a protecting group;
R³ is phenyl or heteroaryl each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^{3E}$,
in which
each L$^{3C}$ is a bond, methylene, ethylene, —C(O)—, —S—, —S(O)$_{1-2}$—, —O—, or —NR$^{3G}$—;
each R$^{3D}$ is independently selected from oxo optionally-substituted C₁-C₄ alkyl, C₁-C₄ fluoroalkyl, halogen, —CN, —SF₅, —N₃, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
each R$^{3E}$ is independently selected from oxo, optionally-substituted C₁-C₄ alkyl, C₁-C₄ fluoroalkyl, halogen, —CN, —SF₅, —N₃, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
each R$^{3F}$ is independently selected from H, C₁-C₃ alkyl and C₁-C₃ fluoroalkyl and
each R$^{3G}$ is independently selected from H, C₁-C₃ alkyl, and C₁-C₃ fluoroalkyl; and
R⁴ is selected from the group consisting of hydrogen, optionally substituted C₁-C₈ alkyl,
optionally-substituted C₁-C₈ alkenyl and optionally substituted C₁-C₈ alkynyl;
wherein
each R⁶ is selected from the group consisting of hydrogen, C₁-C₃ alkyl and —C(O)(C₁-C₃ alkyl);
each optionally substituted alkyl, alkenyl and alkynyl is unsubstituted, fluorinated or substituted with one or two hydroxyl groups;
each cycloalkyl has 3-10 ring carbons and is saturated or partially unsaturated;
each heterocylcloalkyl has 3-10 ring members and 1-3 heteroatoms independently selected from nitrogen, oxygen and sulfur, and is saturated or partially unsaturated; and
each heteroaryl is a 5-6 membered monocyclic heteroaryl ring having 1-3 heteroatoms independently selected from nitrogen, oxygen and sulfur.

7. The compound of claim 6, wherein X is Cl or Br.

8. The compound of claim 6, wherein the halopyrazolylthiazole of formula (Ia) is C₁-C₃ alkyl 1-(4-halo-5-(isopropylthio)thiazol-2-yl)-4-(3-fluorophenyl)-3-methyl-1H-pyrazole-5-carboxylate.

9. A method for preparing a compound of formula (I)

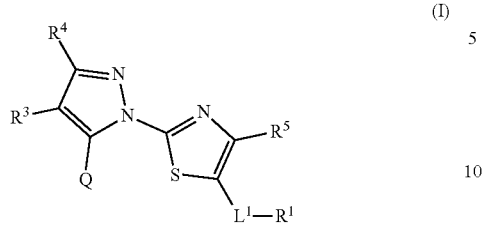

(I)

optionally in the form of a pharmaceutically acceptable salt or N-oxide, and/or a solvate or hydrate, wherein $L^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;

$R^1$ is selected from the group consisting of $C_1$-$C_8$ alkyl, $C_1$-$C_8$ alkenyl and $C_1$-$C_8$ alkynyl, each unsubstituted or fluorinated;

Q is selected from the group consisting of —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —S(O)$_2$R$^{2A}$, —N(R$^{2B}$)S(O)$_2$R$^{2A}$, —S(O)$_2$NR$^{2B}$R$^{2A}$, and —C(O)NH—O(C$_1$-C$_3$ alkyl), in which
each R$^{2A}$ is independently selected from H, $C_1$-$C_3$ alkyl, and a protecting group, and
each R$^{2B}$ is independently selected from H and $C_1$-$C_3$ alkyl;

$R^3$ is phenyl or heteroaryl each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3D}$), -L$^{3C}$-(heterocycloalkyl optionally substituted with 1-5 R$^{3D}$) and (ii) optionally substituted with 1-5 R$^{3E}$,
in which
each L$^{3C}$ is a bond, methylene, ethylene, —C(O)—, —S—, —S(O)$_{1-2}$—, —O—, or —NR$^{3G}$—;
each R$^{3D}$ is independently selected from oxo optionally-substituted $C_1$-$C_4$ alkyl, $C_1$-$C_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
each R$^{3E}$ is independently selected from oxo, optionally-substituted $C_1$-$C_4$ alkyl, $C_1$-$C_4$ fluoroalkyl, halogen, —CN, —SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, and —NR$^{3G}$S(O)$_{1-2}$R$^{3F}$;
each R$^{3F}$ is independently selected from H, $C_1$-$C_3$ alkyl and $C_1$-$C_3$ fluoroalkyl and
each R$^{3G}$ is independently selected from H, $C_1$-$C_3$ alkyl, and $C_1$-$C_3$ fluoroalkyl;

$R^4$ is selected from the group consisting of hydrogen, optionally substituted $C_1$-$C_8$ alkyl, optionally-substituted $C_1$-$C_8$ alkenyl and optionally substituted $C_1$-$C_8$ alkynyl; and $R^5$ is phenyl, heteroaryl, cycloalkyl or heterocycloalkyl, each optionally substituted with 1-5 R$^{5E}$,
in which
each R$^{5E}$ is independently selected from oxo, optionally-substituted $C_1$-$C_4$ alkyl, $C_1$-$C_4$ fluoroalkyl, halogen, —CN, —SF$_5$, —N$_3$, —C(O)R$^{5F}$, —SR$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{5G}$R$^{5F}$, —NR$^{5G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, SC(S)SR$^{5F}$, SC(S)R$^{5F}$, —S(O)$_{1-2}$OR$^{5F}$, —OS(O)$_{1-2}$R$^{5F}$, —S(O)$_{1-2}$NR$^{5G}$R$^{5F}$, and —NR$^{5G}$S(O)$_{1-2}$R$^{5F}$;
each R$^{5F}$ is independently selected from H, $C_1$-$C_3$ alkyl and $C_1$-$C_3$ fluoroalkyl and
each R$^{5G}$ is independently selected from H and $C_1$-$C_3$ alkyl;

wherein
each R$^6$ is selected from the group consisting of hydrogen, $C_1$-$C_3$ alkyl and —C(O)(C$_1$-$C_3$ alkyl);
each optionally substituted alkyl, alkenyl and alkynyl is unsubstituted, fluorinated or substituted with one or two hydroxyl groups;
each cycloalkyl has 3-10 ring carbons and is saturated or partially unsaturated;
each heterocylcloalkyl has 3-10 ring members and 1-3 heteroatoms independently selected from nitrogen, oxygen and sulfur, and is saturated or partially unsaturated;
each heteroaryl is a 5-6 membered monocyclic heteroaryl ring having 1-3 heteroatoms independently selected from nitrogen, oxygen and sulfur, the method comprising:
coupling a halopyrazolylthiazole of formula (Ia)

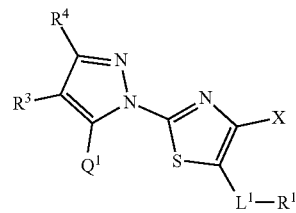

(Ia)

wherein X is a halogen (e.g., Cl, Br or I);

$Q^1$ is selected from the group consisting of —C(O)OR$^{2C}$, —C(O)NR$^{2B}$R$^{2C}$, —C(O)NR$^{2B}$S(O)$_2$R$^{2C}$, —C(O)NR$^{2B}$S(O)$_2$NR$^{2B}$R$^{2C}$, —S(O)$_2$R$^{2C}$, —N(R$^{2B}$)S(O)$_2$R$^{2C}$, —S(O)$_2$NR$^{2B}$R$^{2C}$, and —C(O)NH—O(C$_1$-C$_3$ alkyl), in which
each R$^{2B}$ is independently selected from H and $C_1$-$C_3$ alkyl, and each $R^{2C}$ is independently selected from $C_1$-$C_3$ alkyl and a protecting group;

and $L^1$, $R^1$, $R^3$, and $R^4$ are as described for formula (I), with an organoboron comprising $R^5$ moiety to obtain the compound of formula (I).

10. The method of claim 9, wherein the organoboron is an boronic acid or boronic ester having $R^5$ substituted on the boron atom.

11. The method of claim 10, wherein the organoboron has the formula:

$$Y^1 \underset{B}{\overset{Y^2}{|}} R^5,$$

wherein $R^5$ is as described for formula (I), and $Y^1$ and $Y^2$ are independently hydroxy or $C_1$-$C_4$ alkoxy, or $Y^1$ and $Y^2$ together with B atom form a 5- or 6-membered ring having one or two oxygens in the ring bound to the boron.

12. The method of claim 10, wherein the halopyrazolylthiazole of formula (Ia) and the organoboron are coupled in presence of a palladium catalyst and a base.

13. The method of claim 10, wherein the compound of formula (I) is

[Chemical structure: pyrazole with $R^4$, $R^3$, HOOC substituents, linked to thiazole with $R^5$ and $L^1$—$R^1$]

14. A method for preparing a thiazolylhydrazine of formula (Ib)

[Chemical structure (Ib): $H_2N$-NH-thiazole with X, $L^1$—$R^1$]

wherein

X is a halogen;

$L^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;

$R^1$ is selected from the group consisting of $C_1$-$C_8$ alkyl, $C_1$-$C_8$ alkenyl and $C_1$-$C_8$ alkynyl, each unsubstituted or fluorinated;

wherein each $R^6$ is selected from the group consisting of hydrogen, $C_1$-$C_3$ alkyl and —C(O)($C_1$-$C_3$ alkyl);

the method comprising:

reacting a dihalothiazole of formula

[Chemical structure: thiazole with $X^a$, X, $L^1$—$R^1$]

wherein X, $R^1$, and $L^1$ are as described for formula (Ib), and $X^a$ is halogen, optionally in a solvent, with an aqueous solution of hydrazine to obtain a crude product; and crystallizing the crude product from a hydrocarbon solvent to obtain the thiazolylhydrazine of formula (Ib).

15. The method of claim 14, wherein $X^a$ is chloro or bromo.

16. The method of claim 1, wherein $R^1$ is unsubstituted $C_1$-$C_5$ alkyl or fluorinated $C_1$-$C_5$ alkyl;

$L^1$ is —S—;

$R^3$ is optionally substituted with 1-5 $R^{3E}$, in which each $R^{3E}$ is independently selected from $C_1$-$C_4$ alkyl, $C_1$-$C_4$ fluoroalkyl, halogen, —OR$^{3F}$, and —NR$^{3G}$R$^{3F}$; or wherein $R^{3E}$ is independently selected from halogen, —OR$^{3F}$, and —NR$^{3G}$R$^{3F}$;

$R^4$ is hydrogen or unsubstituted $C_1$-$C_6$ alkyl;

$R^5$ is partially unsaturated cycloalkyl or phenyl, each optionally substituted with 1-5 $R^{5E}$; and $Q^1$ is —C(O)OR$^{2C}$.

17. The method of claim 1, wherein the compound of formula (Ia) is:

[Chemical structure: phenyl with ($R^{3E}$)$_{0-2}$, pyrazole with methyl, $R^CO$-C(=O)-, linked to thiazole with Br and $L^1$—$R^1$]

18. The method of claim 1, wherein the compound of formula (Ia) is:

[Chemical structure: phenyl with ($R^{3E}$)$_{0-2}$, pyrazole with methyl, EtO-C(=O)-, linked to thiazole with Br and $L^1$—$R^1$]

wherein $R^1$ is $C_1$-$C_8$ alkyl, and $R^{3E}$ is independently selected from $C_1$-$C_4$ alkyl, $C_1$-$C_4$ fluoroalkyl, halogen, —OR$^{3F}$, and —NR$^{3G}$R$^{3F}$.

19. Ethyl 1-(4-bromo-5-(isopropylthio)thiazol-2-yl)-4-(3-fluorophenyl)-3-methyl-1H-pyrazole-5-carboxylate.

20. The method of claim 14, wherein $L^1$ is —S— and $R^1$ is isopropyl.

* * * * *